United States Patent
Church et al.

(10) Patent No.: US 6,548,021 B1
(45) Date of Patent: Apr. 15, 2003

(54) SURFACE-BOUND, DOUBLE-STRANDED DNA PROTEIN ARRAYS

(75) Inventors: George M. Church, Brookline, MA (US); Martha L. Bulyk, Brookline, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 09/132,368

(22) Filed: Aug. 11, 1998

Related U.S. Application Data

(60) Provisional application No. 60/061,604, filed on Oct. 10, 1997.

(51) Int. Cl.⁷ .......................... G01N 15/00; G01N 1/00; G01N 33/53; C12Q 1/68; C07H 21/00
(52) U.S. Cl. ...................... 422/68.1; 422/50; 435/4; 435/6; 435/7.1; 435/7.2; 436/501; 536/25.3
(58) Field of Search .................. 435/4–6, 7.1, 7.2; 436/501; 536/22.1, 25.3; 422/50, 68.1

(56) References Cited

U.S. PATENT DOCUMENTS

| | | | |
|---|---|---|---|
| 3,206,317 A | 9/1965 | Golber | 99/192 |
| 3,496,066 A | 2/1970 | Berger et al. | 195/103.5 |
| 3,870,601 A | 3/1975 | Warren et al. | 195/103.5 R |
| 4,129,483 A | 12/1978 | Bochner | 195/100 |
| 4,208,480 A | 6/1980 | D'Amato et al. | 435/34 |

(List continued on next page.)

FOREIGN PATENT DOCUMENTS

| | | |
|---|---|---|
| EP | 0 025 467 | 3/1981 |
| EP | 0059645 | 9/1982 |
| EP | 0332752 | 9/1989 |
| GB | 2 005 410 A | 4/1979 |
| NL | 3419327 | 11/1985 |
| WO | WO 93/17126 | 9/1993 |
| WO | WO 96/36731 | 11/1996 |
| WO | WO 97/10365 | 3/1997 |

OTHER PUBLICATIONS

Jacob et al., Proceedings of the National Academy of Sciences (USA), vol. 86, No. 12, pp. 4669–4673, 1989.*
Brenner et al., "New Medium for the Simultaneous Detection of Total Coliforms and *Escherichia coli* in Water," *Applied and Environmental Microbiology* 59:3534–3544 (1993).
Cabelli et al., "A marine recreational water quality criterion consistent with indicator concepts and risk analysis," *Journal WPCF* 55:1306–1314 (1983).
Cabelli, "Swimming–Associated Illness and Recreational Water Quality Criteria," *Wat. Sci. Tech.*, 21:13–21 (1989).
Dahlen and Linde, "Screening Plate Method for Detection of Bacterial β–Glucuronidase," *Applied Microbiology* 26:863–866 (1973).

(List continued on next page.)

*Primary Examiner*—Ardin H. Marschel
(74) *Attorney, Agent, or Firm*—Banner & Witcoff, Ltd.

(57) ABSTRACT

The invention provides a synthetic array of surface-bound, bimolecular, double-stranded nucleic acid molecules, the array comprising a solid support and a plurality of bimolecular double-stranded nucleic acid molecule members, a member comprising a first nucleic acid strand linked to the solid support and a second nucleic acid strand which is substantially complementary to the first strand and complexed to the first strand by Watson-Crick base pairing, wherein for at least a portion of the members, each member comprises a recognition site within a nucleic acid sequence for a protein, wherein a recognition site within a nucleic acid sequence for a protein of a first member is different from a recognition site within a nucleic acid sequence for a protein of a second member and wherein a protein is bound to a member thereof.

22 Claims, 5 Drawing Sheets

U.S. PATENT DOCUMENTS

| | | | |
|---|---|---|---|
| 4,235,964 A | 11/1980 | Bochner | 435/34 |
| 4,245,043 A | 1/1981 | Lund | 435/33 |
| 4,591,554 A | 5/1986 | Koumura et al. | 435/18 |
| 4,622,297 A | 11/1986 | Kappner et al. | 435/32 |
| 4,675,289 A | 6/1987 | Kanou et al. | 435/18 |
| 4,731,325 A | 3/1988 | Palva et al. | 435/6 |
| 4,803,162 A | 2/1989 | Smith et al. | 435/36 |
| 4,812,409 A | 3/1989 | Babb et al. | 435/7 |
| 4,837,154 A | 6/1989 | Spiegel | 435/253.6 |
| 4,925,789 A | 5/1990 | Edberg | 435/38 |
| 5,004,684 A | 4/1991 | Simpson et al. | 435/8 |
| 5,096,807 A | 3/1992 | Leaback | 435/6 |
| 5,200,051 A | 4/1993 | Cozzette et al. | 204/403 |
| 5,292,644 A | 3/1994 | Berg | 435/29 |
| 5,302,509 A | 4/1994 | Cheeseman | 435/6 |
| 5,306,619 A | 4/1994 | Edwards et al. | 435/6 |
| 5,324,633 A | 6/1994 | Fodor et al. | 435/6 |
| 5,328,825 A | 7/1994 | Warren, III et al. | 435/6 |
| 5,393,662 A | 2/1995 | Roth et al. | 435/38 |
| 5,405,746 A | 4/1995 | Uhlen | 435/6 |
| 5,412,087 A | 5/1995 | McGall et al. | 536/24.3 |
| 5,424,186 A | 6/1995 | Fodor et al. | 435/6 |
| 5,426,180 A | 6/1995 | Kool | 536/25.3 |
| 5,429,933 A | 7/1995 | Edberg | 435/34 |
| 5,437,976 A | 8/1995 | Utermohlen | 435/6 |
| 5,445,934 A | 8/1995 | Fodor et al. | 435/6 |
| 5,484,702 A | 1/1996 | Ludwig | 435/6 |
| 5,510,270 A | 4/1996 | Fodor et al. | 436/518 |
| 5,527,681 A | 6/1996 | Holmes | 435/6 |
| 5,545,531 A | 8/1996 | Rava et al. | 435/6 |
| 5,552,270 A | 9/1996 | Khrapko et al. | 435/6 |
| 5,556,752 A | 9/1996 | Lockhart et al. | 435/6 |
| 5,571,639 A | 11/1996 | Hubbell et al. | 430/5 |
| 5,578,444 A | 11/1996 | Edwards et al. | 435/6 |
| 5,578,832 A | 11/1996 | Trulson et al. | 250/458.1 |
| 5,587,128 A | 12/1996 | Wilding et al. | 422/50 |
| 5,593,839 A | 1/1997 | Hubbell et al. | 435/6 |
| 5,599,695 A | 2/1997 | Pease et al. | 435/91.1 |
| 5,616,478 A | 4/1997 | Chetverin et al. | 435/91.2 |
| 5,631,134 A | 5/1997 | Cantor | 435/6 |
| 5,641,658 A | 6/1997 | Adams et al. | 435/91.2 |
| 5,653,939 A | 8/1997 | Hollis et al. | 422/50 |
| 5,753,439 A * | 5/1998 | Smith et al. | 435/6 |
| 5,770,722 A * | 6/1998 | Lockhart et al. | 536/25.3 |
| 5,800,992 A * | 9/1998 | Fodor et al. | 435/6 |

OTHER PUBLICATIONS

Damare et al., "Simplified Direct Plating Method for Enhanced Recovery of *Escherichia coli* on Food," *J. Food Science* 50:1736–1738 (1985).

Donnelly and Hartman, "Gentamicin–Based Medium for the Isolation of Group D Streptococci and Application of the Medium to Water Analysis," *Applied And Environmental Microbiology* 35:576–581 (1978).

Edberg et al., "National Field Evaluation of a Defined Substrate Method for the Simultaneous Enumeration of Total Coliforms and *Escheria coli* from Drinking Water: Comparison with Standard Multiple Tube Fermentation Method," *Applied and Environmental Microbiology* 54:1595–1601 (1988).

Edberg and Kontnick, "Comparison of G–Glucuronidase–Based Substrate Systems for Identification of *Escherichia coli*," *J. Clinical Microbiology* 24:368–371 (1986).

Feng and Hartman, "Fluorogenic Assays for Immediate Confirmation of *Escheria coli*," *Applied and Environmental Microbiology* 43:1320–1329 (1982).

Gatti and Neviani, "A New Simple Medium for the Detection of *Enterococcus Faecalis And Enterococcus Faecium* by Measurement of Conductance Changes," *Letters in Applied Microbiology* 17:72–74 (1993).

Hansen and Yourassowsky, "Detection of β–Glucuronidase in Lactose–Fermenting Members of the *Family Enterobacteriaceae* and Its Presence in Bacterial Urine Cultures," *J. Clin. Microbiol.* 20:1177–1179.

Hernandez et al., "MPN Miniaturized Procedure for the Enumeration of Faecal Enterococci in Fresh and Marine Waters: The Must Procedure," *Wat. Res.* 27:597–606 (1993).

Kendall et al., "Observations of the Relative Constancy of Ammonia Production by Certain Bacteria," *J. Infectious Diseases* 13:425–428 (1913).

Knutson and Hartman,, "Comparison of Fluorescent Gentamicin–Thallous–Carbonate and KF Streptococcal Agars to Enumerate Enterococci and Fecal Streptococci in Meats," *Applied and Environmental Microbiology* 59:936–938.

Littel and Hartman, "Fluorogenic Selective and Differential Medium for Isolation of Fecal Streptococci," *Applied and Environmental Microbiology* 45:622–627 (1983).

Maddocks and Greenan, "Technical Method: A rapid method for identifying bacterial enzymes," *J. Clinical Pathology* 23:686–687 (1975).

Robison, B., "Evaluation of a Fluorogenic Assay for Detection of *Escheria coli* in foods," *Applied and Environmental Microbiology* 48:285–288 (1984).

Sarhan and Foster, "A rapid fluorogenic method for the detection of *Escherichia coli* by the production of fl–glucuronidase," *J. Applied Bacteriology* 70:394–400 (1991).

Thomas, Jr., "Bacterial Densities From Fermentation Tube Tests," *J. Am. Water Works Assoc.* 34:572–576 (1942).

Trepeta and Edberg, Methylumbelliferyl–,β–D–Glucuronide–Based Medium for Rapid Isolation and Identification of *Escherichia coli, J. Clinical Microbiology* 19:172–174 (1984).

Ur and Brown, "Impedance Monitoring of Bacterial Activity," *J. Med. Microbiol.* 8:19–28 (1975).

* cited by examiner

SURFACE-BOUND, DOUBLE-STRANDED DNA PROTEIN ARRAYS

This application claims the benefit of U.S. Provisional Application No. 60/061,604, filed Oct. 10, 1997, now abandoned.

This invention was supported by DOE Grant No. DEFG02-87ER-60565 and the U.S. government has certain rights to the invention.

FIELD OF INVENTION

The invention relates to nucleic acid protein arrays.

BACKGROUND OF THE INVENTION

Compact arrays or libraries of surface-bound, double-stranded oligonucleotides are of use in rapid, high-throughput screening of proteins to identify those that bind, or otherwise interact with, short, double-stranded DNA sequence motifs. Of particular interest are trans-regulatory factors that control gene transcription. Ideally, such an oligonucleotide array is bound to the surface of a solid support matrix that is of a size that enables laboratory manipulations, e.g. an incubation of a candidate protein with the nucleic acid sequences thereon, and that is itself inert to chemical interactions with experimental proteins, buffers and/or other components. In addition, it is desirable that the absolute number of unique nucleic acid sequences in the array be maximized, since methods of high-throughput screening are used in the attempt to minimize repetition of steps that are labor-intensive or otherwise costly.

A high-density, double-stranded DNA array complexed to a solid matrix is described by Lockhart (U.S. Pat. No. : 5,556,752); however, the DNA molecules therein disclosed are produced as unimolecular products of chemical synthesis. As synthesized, each member of the array contains regions of self-complementarity separated by a spacer (i.e. a single-strand loop), such that these regions hybridize to each other in order to produce a double-helical region. Further, it is required that those regions of complementary nucleic acid sequences that must hybridize in order to form the double-helical structure are physically attached to each other by a linker subunit.

SUMMARY OF THE INVENTION

The invention provides a synthetic array of surface-bound, bimolecular, double-stranded nucleic acid molecules, the array comprising a solid support and a plurality of bimolecular double-stranded nucleic acid molecule members, a member comprising a first nucleic acid strand linked to the solid support and a second nucleic acid strand which is substantially complementary to the first strand and complexed to the first strand by Watson-Crick base pairing, wherein for at least a portion of the members, each member comprises a recognition site within a nucleic acid sequence for a protein, wherein a recognition site within a nucleic acid sequence for a protein of a first member is different from a recognition site within a nucleic acid sequence for a protein of a second member and wherein a protein is bound to a member thereof.

The term "synthetic", as used herein, is defined as that which is produced by in vitro chemical or enzymatic synthesis. The synthetic arrays of the present invention may be contrasted with natural nucleic acid molecules such as viral or plasmid vectors, for instance, which may be propagated in bacterial, yeast, or other living hosts.

As used herein, the term "nucleic acid" is defined to encompass DNA and RNA or both synthetic and natural origin. The nucleic acid may exist as single- or double-stranded DNA or RNA, an RNA/DNA heteroduplex or an RNA/DNA copolymer, wherein the term "copolymer" refers to a single nucleic acid strand that comprises both ribonucleotides and deoxyribonucleotides.

As used herein, the term "bimolecular" refers to the fact that the 5' end of the first strand and 3' end of the second strand are not linked via a covalent bond, and thus do not form a continuous single strand. As used herein in this context, "covalent bond" is defined as meaning a bond that forms, directly or via a spacer comprising nucleic acid or another material, a continuous strand that comprises the 5' end of the first strand and the 3' end of the second strand, and thus includes a 3'/5' phosphate bond as occurs naturally in a single-stranded nucleic acid. This definition does not encompass intermolecular crosslinking of the first and second strands.

When used herein in this context, the term "double-stranded" refers to a pair of nucleic acid molecules, as defined above, that exist in a hydrogen-bonded, helical array typically associated with DNA, and that under these umbrella terms are included those paired oligonucleotides that are essentially double-stranded, meaning those that contain short regions of mismatch, such as a mono-, di- or tri-nucleotide, resulting from design or error either in chemical synthesis of the oligonucleotide priming site on the first nucleic acid strand or in enzymatic synthesis of the second nucleic acid strand; it is contemplated that at least a portion of the members of the array have a second nucleic acid strand which is substantially complementary to- and base paired with the first strand along the entire length of the first strand.

As used herein, the terms "complementary" and "substantially complementary" refer to the hybridization or base pairing between nucleotides or nucleic acids, such as, for instance, between the two strands of a double-stranded DNA molecule or between an oligonucleotide primer and a primer binding site on a single stranded nucleic acid to be sequenced or amplified. Complementary nucleotides are, generally, A and T (or A and U), or C and G. Typically, sequences which are complementary will hybridize to each other under stringent conditions. Stringent hybridization conditions will typically include salt concentrations of less than about 1M, more usually less than about 500 mM, and preferably less than about 200 mM. Alternatively, stringent hybridization conditions typically include at least 10% formamide, preferably 20% and more preferably 40%. Hybridization temperatures can be as low as 5° C., but are typically greater than 22° C., more typically greater than about 30° C., and preferably in excess of about 37° C. Longer fragments may require higher hybridization temperatures for specific hybridization, while those that are rich in dA and dT may require lower temperatures. Two single-stranded RNA or DNA molecules are said to be substantially complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. Sequences that are substantially complementary may hybridize under stringent conditions; however, it is usually necessary to raise the concentration of salt, or lower the concentration of formamide or the hybridization temperature.

As used herein in reference to nucleic acid members of an array, the term "portion" refers to at least two members of an array. Preferably, a portion refers to a number of individual members of an array, such as at least 60%, 80%, 90% and 95–100% of such members.

As used herein, the terms "recognition site for a protein" and "recognition site within a nucleic acid sequence for a protein" refers to a nucleic acid sequence which is recognized and/or bound by a protein.

As used herein with regard to recognition sites within a nucleic acid sequence for a protein, the term "different" refers to two or more nucleic acid sequences which are recognized and/or bound by a protein or proteins, which recognition sites within a nucleic acid sequence for a protein differ in the identity of at least one nucleotide.

As used herein, the term "array" is defined to mean a heterogeneous pool of nucleic acid molecules that is affixed to a solid support in a spatially-ordered manner, such as a Cartesian distribution (in other words, arranged at defined points along the x- and y axes of a grid or specific 'clock positions' within- or degrees or radii from the center of a radial pattern) of nucleic acid molecules over the support, that permits identification of individual features during the course of experimental manipulation.

As used herein, the term "feature" refers to each nucleic acid sequence occupying a discrete physical location on the array; if a given sequence is represented at more than one such site, each site is classified as a feature. A feature comprises one or a plurality of individual, double-stranded, bimolecular nucleic acid molecule members; within a given feature, every such member represents the same sequence.

According to the invention, the array may have virtually any number of different features. In preferred embodiments, the array comprises from 2 up to 100 features, more preferably from 100 up to 10,000 features and highly preferably from 10,000 up to 1,000,000 features, preferably on a solid support. In preferred embodiments, the array will have a density of more than 100 features at known locations per $cm^2$, preferably more than 1,000 per $cm^2$, more preferably more than 10,000 per $cm^2$.

According to the methods disclosed herein, a "solid support" (or, simply, "support") is defined as a material having a rigid or semi-rigid surface to which nucleic acid molecules may be attached or upon which they may be synthesized.

It is contemplated that attached to the solid support is a spacer. The spacer molecule is preferably of sufficient length to permit the double-stranded oligonucleotide in the completed member of the array to interact freely with molecules exposed to the array. The spacer molecule, which may comprise as little as a covalent bond length, is typically 6–50 atoms long to provide sufficient exposure for the attached double-stranded DNA molecule. The spacer is comprised of a surface attaching portion and a longer chain portion.

It is preferred that the 3' end of the first strand is linked to the support.

It is additionally preferred that the 5' end of the first strand and the 3' end of the second strand are not linked via a covalent bond.

Preferably, the 5' end of the second strand is not linked to the support.

It is preferred that the recognition site within a nucleic acid sequence for a protein is selected from the group that includes naturally-occurring recognition sites within a nucleic acid sequence for a protein or proteins, synthetic variants of naturally-occurring recognition sites within a nucleic acid sequence for a protein or proteins and randomized nucleic acid sequences.

As used herein in reference to recognition sites within a nucleic acid sequence for a protein or proteins, the term "naturally-occurring" refers to such sequences isolated from an organism, wherein those sequences are native to that species or strain of organism and are not the products of genetic engineering, e.g. synthetic sequences, whether transiently transfected or stably incorporated into the genome of a transgenic or transiently-transfected organism or one or more of its ancestor organisms.

As used herein, the term "allelic variant" refers to a naturally-occuring nucleic acid sequence which is present in a subset of individuals (2–98%) of a population. Such a sequence may function properly (e.g. be recognized by the correct protein) or may be poorly- or non-functional. The term "poorly-functional" refers to a recognition site within a nucleic acid sequence for a protein which, for example, has lowered affinity for its corresponding protein or is recognized and bound by the wrong protein. In this context, a "non-functional" recognition site within a nucleic acid sequence for a protein would be expected to bind background levels of (essentially no) protein. Unless found in a majority of individuals in a population, the sequence of an allelic variant differs in at least one position relative to that of a consensus sequence, as defined below.

As used herein, the term "mutant variant" refers to a naturally-occurring nucleic acid sequence which occurs at a low frequency (less than 2%) in a population. As is true of an allelic variant, a mutant variant may function properly, poorly or not at all.

As used herein, the term "synthetic variant" refers to a nucleic acid sequence in which the identity of at least one nucleotide has been altered in vitro, such that it represents no naturally-occuring variant of the sequence upon which is is based. A synthetic variant may function properly, poorly or not at all.

As used herein with regard to individual nucleic acid sequences, the term "randomized" refers to in vitro-synthesized sequences in which any nucleotide or ribonucleotide can be present at one, more than one or all positions; therefore, for such positions as are randomized, the sequence of the finished molecule is not predetermined, but is left to chance.

As used herein with regard to an array of the invention, the term "randomized" refers to an array which is constructed such that, for a sequence of a recognition site within a nucleic acid sequence of a protein of a selected length (e.g. a hexamer), each possible nucleotide combination is comprised by a corresponding feature thereof. In order to realize a complete set of such nucleotide sequence permutations, it is necessary to specify fully the sequence of each feature during synthesis of the array; therefore, while such an array may be referred to as an "array of randomized 6-mers" the design of the array is entirely non-random.

One or more recognition sites within a nucleic acid sequence for a protein or proteins may be present in a given member nucleic acid of an array, wherein "one or more" refers to one, two, three, four, five and even up to 10–20 sites.

In a preferred embodiment, the recognition site within a nucleic acid sequence for a protein comprises two half-sites, wherein either is recognized by a different protein than is the other.

As used herein, the term "half-site" refers to a nucleic acid sequence which is recognized and bound by a targeting amino acid sequence present on one protein subunit of a dimeric protein complex. Neither subunit of the dimeric protein complex will bind its cognate half-site alone (i.e., unless dimerized to the other); therefore, either both half-sites are occupied by protein, or neither is. Both half sites of a recognition site within a nucleic acid sequence for a protein may be identical, whether arranged head-to-tail or as a palindrome (head-to-head or tail-to-tail); if in the latter configuration, the sequence of a recognition site within a nucleic acid sequence of a protein is said to have "dyad symmetry". Typically, a recognition site within a nucleic acid sequence for a protein bound by a protein homodimer comprises two identical half-sites. Alternatively, the two half-sites comprised by a recognition site within a nucleic acid sequence for a protein may be unlike in sequence; it is usually true that dissimilar half-sites are bound by different targeting amino acid sequences, as would be found on the two subunits of a protein heterodimer. Depending on their orientation relative to one another, recognition sites within a nucleic acid sequence for a protein comprising non-identical, but similar, half-sites may also be said to have dyad symmetry.

As used herein, the term "targeting amino acid sequence" refers to an amino acid sequence present on a protein which sequence recognizes a recognition site within a nucleic acid sequence for a protein on a nucleic acid molecule. A protein may comprise one or a plurality (two or more) of targeting amino acid sequences and bind one or a plurality of different recognition sites within a nucleic acid sequence for a protein or proteins. A given targeting nucleic acid sequence may recognize and bind one recognition site within a nucleic acid sequence for a protein or different recognition sites within a nucleic acid sequence for a protein or proteins on a nucleic acid molecule. "Different targeting amino acid sequences", herein defined as those which differ by at least one amino acid, may recognize and bind the same recognition site within a nucleic acid sequence for a protein or proteins, different recognition sites within a nucleic acid sequence or sequences for a protein or proteins, or two partially-overlapping sets of different recognition sites within a nucleic acid sequence for a protein or proteins on a nucleic acid molecule.

It is contemplated that different targeting amino acid sequences, as defined above, may exist on a single polypeptide molecule; typically, however, different targeting amino acid sequences are found on different polypeptide molecules that are of use in the invention. If a polypeptide should possess two or more targeting amino acid sequences, and these targeting amino acid sequences differ in the sequence of at least one amino acid (whether or not they differ in binding-site specificity), that single polypeptide molecule comprises more than one different protein, as defined herein.

The term "half-site" is not applicable to a recognition site within a nucleic acid sequence for a protein (whether in whole or in part) which is recognized by a protein that binds nucleic acids alone, rather than in a di- or multimeric complex, regardless of the presence of any internal symmetry or repetition of sequence in such a recognition site within a nucleic acid sequence for a protein.

As used herein, the term "different protein" refers to two or more proteins which differ in the identity of at least one amino acid within a targeting amino acid sequence.

It is contemplated that different recognition sites within a nucleic acid sequence for a protein on a nucleic acid molecule or molecules may be recognized and bound by the same targeting amino acid sequence, by different targeting amino acid sequences, or by two partially-overlapping sets of different targeting amino acid sequences of a protein or proteins.

It is preferred that the protein which is bound to a member thereof comprises a detectable label.

Preferably, the protein is a chimeric protein.

As used herein, the term "chimeric" refers to a protein which comprises fused sequences of two or more polypeptides that are, themselves, different in amino acid sequence and are typically encoded by different genes. The term "different genes" may refer to allelic of mutant variants of a gene present at a single genetic locus; preferably, it refers to two or more genes which are found at a corresponding number of genetic loci, and which may be selected from one or more individual organisms or species of organism. A chimeric protein may be advantageously produced by the in-frame fusion and subsequent expression of nucleic acid sequences encoding the component amino acid sequences. Such amino acid sequences may each comprise an entire protein; alternatively, one or more sequence comprised by a chimeric protein may be a fragment of a protein. Typically, each segment is sufficient in scope to retain its native biological activity (e.g. a targeting amino acid sequence which binds a recognition site within a nucleic acid sequence for a protein on a nucleic acid molecule in the context of its native protein will do so in the context of the chimera).

It contemplated that a chimeric (or "fusion") protein according to the invention comprises a protein which binds a recognition site within a nucleic acid sequence for a protein, fused to a second protein component comprising any one of a receptor, an enzyme, a candidate enzyme domain such as a kinase or a protease domain, a candidate protein:protein dimerization domain, a candidate ligand binding domain, or a substrate for a protein-directed enzymatic reaction. In this context, a "protein" is either a whole protein or a protein fragment which retains its ability to recognize- and bind specifically to a recognition site within a nucleic acid sequence for a protein on a nucleic acid molecule to which site the native, whole protein binds.

As used herein, the term "domain" is a portion of a protein molecule which is sufficient for the performance of a given function, whether in the presence or absence of other sequences of the protein. It is contemplated that a domain is encoded by an uninterrupted amino acid sequence, such that it may be physically cleaved whole away from other amino acid sequence elements and such that it will fold properly without the influence of neighboring sequences.

It is preferred that the chimeric protein comprises a DNA-binding domain fused in-frame with a protein:protein dimerization domain.

As used herein with regard to protein domains, the term "DNA-binding" refers to a function of the domain, which is to bind to a recognition site within a nucleic acid sequence for a protein on a DNA molecule.

In another preferred embodiment, the chimeric protein comprises a DNA-binding domain fused in-frame to Green Fluorescent Protein.

Preferably, the solid support is a silica support.

It is preferred that the first strand is produced by chemical synthesis and the second strand is produced by enzymatic synthesis.

Preferably, the first strand is used as the template on which the second strand is enzymatically produced.

It is preferred that the first strand of each member contains at its 3' end a binding site for an oligonucleotide primer which is used to prime enzymatic synthesis of the second strand, and at its 5' end a variable sequence.

The term "oligonucleotide primer", as used herein, refers to a single-stranded DNA or RNA molecule that is hybridized to a nucleic acid template to prime enzymatic synthesis of a second nucleic acid strand.

Preferably, enzymatic synthesis is performed using an enzyme.

In a preferred embodiment, the oligonucleotide primer is between 10 and 30 nucleotides in length.

It is preferred that the first strand comprises DNA.

It is additionally preferred that the second strand comprises DNA.

Preferably, the first and second strands each comprise from 16 to 60 monomers selected from the group that includes ribonucleotides and deoxyribonucleotides.

Use of the term "monomer" is made to indicate any of the set of molecules which can be joined together to form an oligomer or polymer. The set of monomers useful in the present invention includes, but is not restricted to, for the example of oligonucleotide synthesis, the set of nucleotides consisting of adenine, thymine, cytosine, guanine, and uridine (A, T, C, G, and U, respectively) and synthetic analogs thereof. As used herein, "monomer" refers to any member of a basis set for synthesis of an oligomer. Different basis sets of monomers may be used at successive steps in the synthesis of a polymer.

Preferably, at least a portion of the plurality have a second nucleic acid strand that is substantially complementary to- and base-paired with the first strand along the entire length of the first strand.

As used herein in reference to a plurality of nucleic acid members of an array, the term "portion" refers to at least two members of an array. Preferably, a portion refers to a number of individual members of an array, such as at least 60%, 80%, 90% and 95–100% of such members.

Another aspect of the present invention is a method for the construction of a synthetic array of surface-bound, bimolecular, double-stranded nucleic acid molecules, comprising the steps of providing an array of first nucleic acid strands linked to a solid support, hybridizing to the first strands an oligonucleotide primer that is substantially complementary to a sequence comprised by a first strand, performing enzymatic synthesis of a second nucleic acid strand that is complementary to a first strand so as to permit Watson-Crick base pairing and so as to form an array comprising a plurality of bimolecular, double-stranded nucleic acid molecule members, wherein for at least a portion of the members, each member comprises a recognition site within a nucleic acid sequence for a protein and wherein a recognition site within a nucleic acid sequence for a protein of a first member is different from a recognition site within a nucleic acid sequence for a protein of a second member, and incubating the array with a protein sample comprising a protein under conditions that permit specific binding of the protein to a member of the array, such that a protein becomes bound to a recognition site within a nucleic acid sequence for a protein on a member to form a nucleic acid protein array.

Preferably, the 3' end of the first strand is linked to the support.

It is preferred that the 5' end of the first strand and the 3' end of the second strand are not linked via a covalent bond.

It is additionally preferred that the 5' end of the second strand is not linked to the solid support.

Preferably, the recognition site within a nucleic acid sequence for a protein is selected from the group that includes naturally-occurring recognition sites within a nucleic acid sequence for a protein or proteins, synthetic variants of naturally-occurring recognition sites within a nucleic acid sequence for a protein or proteins and randomized nucleic acid sequences.

Preferably, the recognition site within a nucleic acid sequence for a protein comprises two half-sites, wherein either is recognized by a different protein than is the other.

It is preferred that the protein which is bound to a member of the array comprises a detectable label.

It is also preferred that the protein is a chimeric protein.

In a particularly preferred embodiment, the chimeric protein comprises a DNA-binding domain fused in-frame with a protein:protein dimerization domain.

It is also particularly preferred that the chimeric protein comprises a DNA-binding domain fused in-frame to Green Fluorescent Protein.

Preferably, the solid support is a silica support.

It is preferred that the first strand of each member contains at its 3' end a binding site for an oligonucleotide primer which is used to prime enzymatic synthesis of the second, and at its 5' end a variable sequence, wherein the binding site is present in each member of the array.

Preferably, enzymatic synthesis is performed using an enzyme.

In a preferred embodiment, the oligonucleotide primer of is between 10 and 30 nucleotides in length.

It is preferred that the first strand comprises DNA.

It is additionally preferred that the second strand comprises DNA.

Preferably, the first and second strands each comprise from 16 to 60 monomers selected from the group that includes ribonucleotides and deoxyribonucleotides.

In a highly preferred embodiment, the solid support is a silica support and the first and second strands each comprise from 16 to 60 monomers selected from the group that includes ribonucleotides and deoxyribonucleotides.

Preferably, the protein sample comprises a candidate inhibitor of binding of the protein to a recognition site within a nucleic acid sequence for a protein on a member of the array.

It is preferred that the protein sample comprises a candidate inhibitor of binding of the protein to a second protein.

The invention also encompasses a method of determining a consensus nucleic acid sequence for a recognition site within a nucleic acid sequence in a nucleic acid molecule for a protein comprising the steps of providing a nucleic acid protein array comprising a solid support and a plurality of bimolecular double-stranded nucleic acid molecule members, a member comprising a first nucleic acid strand linked to the solid support and a second nucleic acid strand which is substantially complementary to the first strand and complexed to the first strand by Watson-Crick base pairing, wherein for at least a portion of the members, each member comprises a recognition site within a nucleic acid sequence for a protein, wherein a recognition site within a nucleic acid sequence for a protein of a first member is different from a recognition site within a nucleic acid sequence for a protein of a second member and wherein a protein comprising a detectable label is bound to a member thereof, and performing a detection step to detect the presence of the label on a feature of the array, wherein nucleotides that are shared among the recognition sites within a nucleic acid sequence for a protein present on features on which the label is detected form a consensus nucleic acid sequence for a recognition site within a nucleic acid sequence for a protein specific for the protein.

As defined herein in reference to recognition sites within a nucleic acid sequence for a protein or proteins, the term "consensus" refers to a common nucleic acid sequence wherein the nucleotide at each position thereof represents that which is most frequently found in recognition sites within a nucleic acid sequence for a selected protein or group of proteins. A consensus sequence may be identical to a naturally-occurring recognition site within a nucleic acid sequence for a protein; alternatively, it may have a sequence which does not occur naturally in the genome of an organism.

As used herein, the term "shared" refers to a nucleotide or ribonucleotide which is present in all, or substantially all sequences compared, wherein substantial sharing is defined as the presence in 75% or more of said sequences of a given nucleotide or ribonucleotide at a specified position.

The invention additionally provides a method of identifying for a first protein which binds a nucleic acid as half of a protein:protein heterodimer complex one or a plurality of candidate second proteins with which it might dimerize and bind a nucleic acid molecule in vivo, comprising the steps of providing a nucleic acid array comprising a solid support and a plurality of bimolecular double-stranded nucleic acid molecule members, a member comprising a first nucleic acid strand linked to the solid support and a second nucleic acid strand which is substantially complementary to the first strand and complexed to the first strand by Watson-Crick base pairing, wherein for at least a portion of the members, each member comprises a recognition site within a nucleic acid sequence for a protein, wherein a recognition site within a nucleic acid sequence for a protein of a first member is different from a recognition site within a nucleic acid sequence for a protein of a second member, wherein a binding site comprises two half-sites and wherein either of the half-sites of a recognition site within a nucleic acid sequence for a protein is recognized by a different protein than is the other, incubating the array with a protein sample comprising a first protein which recognizes a first half-site of a recognition site within a nucleic acid sequence within a nucleic acid sequence for a protein and one or a plurality of candidate second proteins under conditions which permit heterodimerization of a first and candidate second protein and binding of a protein:protein heterodimer to a recognition site within a nucleic acid sequence for a protein, recovering a protein:protein heterodimer complex from a member of the array under conditions whereby the first protein and candidate second protein dissociate from one another, and identifying the candidate second protein, wherein each candidate second protein so identified represents a protein with which the first protein may dimerize in vivo.

Preferably, identifying of the candidate second protein comprises sequencing thereof.

In another preferred embodiment, identifying of the candidate second protein comprises binding of the candidate second protein to an antibody which is specific therefor.

It is preferred that the first protein comprises a detectable label.

It is additionally preferred that the method further comprises the step of performing a detection step to detect the presence of the label on a feature of the array, wherein the recognition site within a nucleic acid sequence for a protein present on a feature upon which the label is detected represents a candidate recognition site within a nucleic acid sequence for a protein which the heterodimer may bind in vivo.

The invention also provides a method of identifying candidate members of a set of co-regulated genes, comprising the steps of providing a nucleic acid protein array comprising a solid support and a plurality of bimolecular double-stranded nucleic acid molecule members, a member comprising a first nucleic acid strand linked to the solid support and a second nucleic acid strand which is substantially complementary to the first strand and complexed to the first strand by Watson-Crick base pairing, wherein for at least a portion of the members, each member comprises a recognition site within a nucleic acid sequence for a protein, wherein a recognition site within a nucleic acid sequence for a protein of a first member is different from a recognition site within a nucleic acid sequence for a protein of a second member and wherein a protein comprising a detectable label is bound to a member thereof, and performing a detection step to detect the presence of the label on a feature of the array, wherein a gene having among its regulatory sequences one or more of the recognition sites within a nucleic acid sequence for a protein present on a feature on which the label is detected is characterized as a candidate member of a set of co-regulated genes that are regulated by the protein.

A "set of co-regulated genes" refers to a number of genes, in the range of about 2 to about 30 genes, that exhibit a given response (in terms of gene expression) to an external stimulus or a given response to a mutation in a specific gene. An example of the latter is where a mutation in the coding region of gene X results in a change in expression levels of genes A–Z. The term "co-regulated set of genes" additionally encompasses genes which are normally under the control of a common trans-regulatory factor, such as a protein. The upper limit on the number in a set of co-regulated genes (i.e., "positives" or up-regulated genes; or "negatives" or down-regulated genes) may be on the order of several thousand.

Another aspect of the present invention is a method of assaying a candidate inhibitor of protein/nucleic acid interactions, comprising the steps of providing a nucleic acid array comprising a solid support and a plurality of bimolecular double-stranded nucleic acid molecule members, a member comprising a first nucleic acid strand linked to the solid support and a second nucleic acid strand which is substantially complementary to the first strand and complexed to the first strand by Watson-Crick base pairing, wherein for at least a portion of the members, each member comprises a recognition site within a nucleic acid sequence for a protein, wherein a recognition site within a nucleic acid sequence for a protein of a first member is different from a recognition site within a nucleic acid sequence for a protein of a second member, incubating the array with a protein sample comprising a protein comprising a detectable label and a candidate inhibitor of binding of the protein to a recognition site within a nucleic acid sequence for a protein on a member of the array, under conditions which normally permit binding of the protein to that member, and performing a detection step to detect the presence of the label on the member, wherein the presence of the label on the member corresponds with binding of the protein to the member and wherein the negation of- or reduction in binding of the protein to the member is indicative of efficacy of the candidate inhibitor of protein:nucleic acid interactions in inhibiting binding of the protein to the recognition site within a nucleic acid sequence for a protein.

Such protein:nucleic interactions include, but are not limited to, recognition of cis-regulatory elements by transcription factors, which may include receptors or polymerase subunits, binding of nucleic acid molecules by structural proteins, such as histones or cytoskeletal components, and recognition of a nucleic acid molecule by restriction- or other endonucleases, exonucleases and nucleic acid modification enzymes (such as methylases, ligases, phospatases, isomerases, transposases or other recombinases, glycosylases and kinases).

The final aspect of the present invention is a method of assaying a candidate inhibitor of a protein/protein interaction, comprising the steps of providing a nucleic acid array comprising a solid support and a plurality of bimolecular double-stranded nucleic acid molecule members, a member comprising a first nucleic acid strand linked to the solid support and a second nucleic acid strand which is substantially complementary to the first strand and complexed to the first strand by Watson-Crick base pairing, wherein for at least a portion of the members, each member comprises a recognition site within a nucleic acid sequence for a protein, wherein a recognition site within a nucleic acid sequence for a protein of a first member is different from a recognition site within a nucleic acid sequence for a protein of a second member, incubating the array with a protein sample comprising a first protein comprising a detectable label, wherein binding of the first protein to a recognition site within a nucleic acid sequence for a protein on a member of the array is dependent upon an interaction between the first protein and a second protein and wherein the protein sample further comprises the second protein and a candidate inhibitor of the interaction, under conditions which normally permit the interaction, and performing a detection step to detect the presence of the label on a member of the array, wherein the presence of the label on a member corresponds with binding of the protein to that member and wherein the negation of- or reduction in binding of the protein to the member is indicative of efficacy of the candidate inhibitor in inhibiting the interaction between the first protein and the second protein.

Such protein:protein interactions include, but are not limited to, ligand/receptor interactions, enzyme/substrate interactions, interactions between subunits of a nucleic acid polymerase, and interactions between molecules of homo- or heterodimeric or -multimeric complexes.

The utilization of bimolecular, double-stranded, nucleic acid arrays comprising recognition sites within a nucleic acid sequence for a protein or proteins or that of nucleic acid/protein arrays according to the invention provides an improvement over prior art methods in that while the first strand of the DNA duplex is chemically-synthesized on the support matrix, the second strand is enzymatically produced using the first strand as a template. While the error rate in production of the first strand remains the same, increased fidelity of second strand synthesis is expected to result in a higher percentage of points on the matrix surface that are filled by hybridized DNA duplex molecules that can serve as targets for protein binding- or other assays. In addition, oligonucleotide priming of second nucleic acid strand synthesis obviates the need for covalent linkage of complementary regions, with the effect of reducing extraneous sequence or non-nucleic acid material from the array, as well as eliminating steps of designing and synthesizing such a linker.

Further features and advantages of the invention will become more fully apparent in the following description of the embodiments and drawings thereof, and from the claims.

DESCRIPTION OF THE INVENTION

Double-Stranded-Protein Arrays According to the Invention

Figure 1:
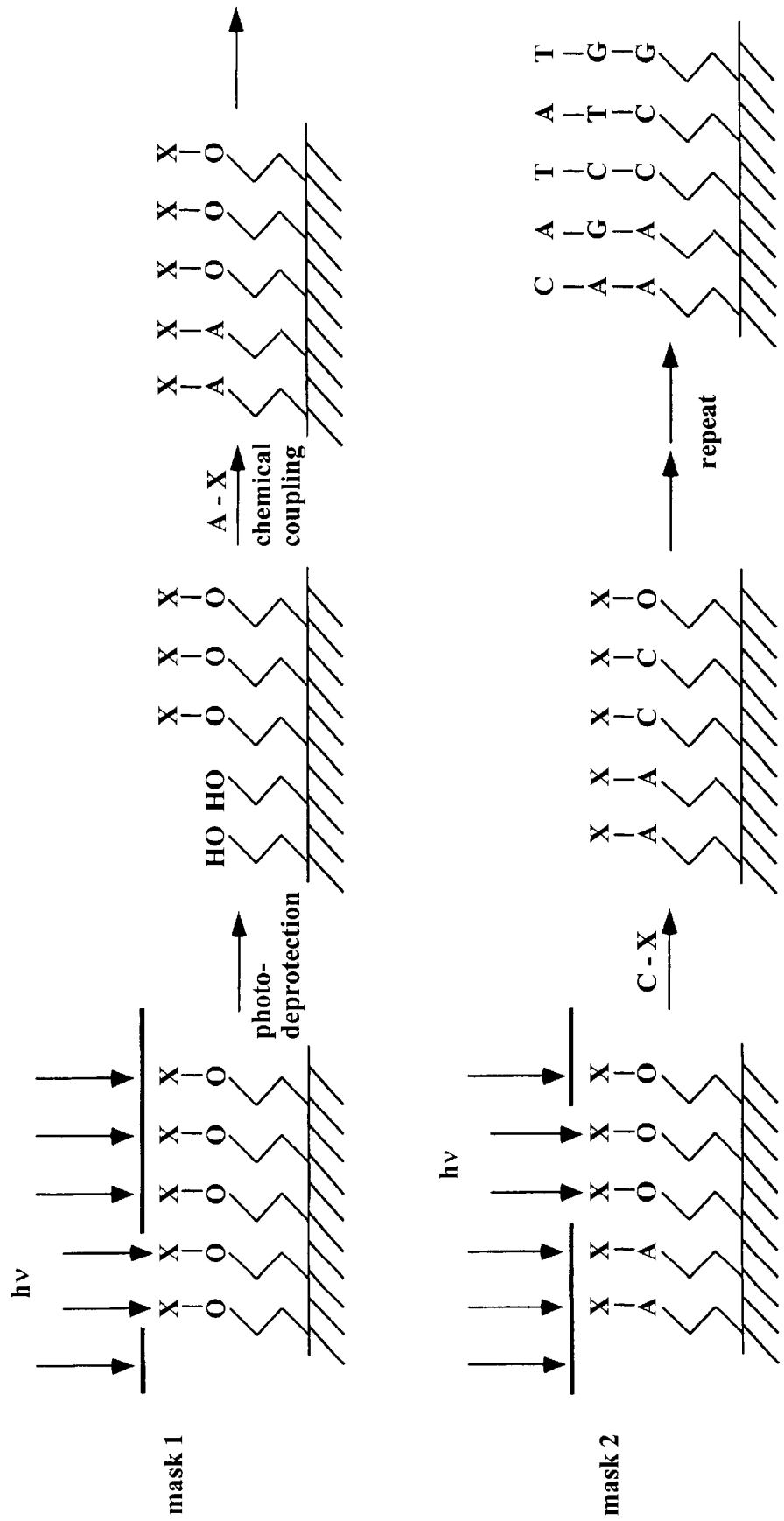
FIG. 1 presents a schematic summary of light-directed DNA synthesis.

The invention is based on double-stranded nucleic acid molecule protein arrays, wherein at least two double-stranded nucleic acid molecules contain one or more recognition sites within a nucleic acid sequence for a protein, such that a recognition site within a nucleic acid sequence of a first member of the array is different from a recognition site within a nucleic acid sequence of a second member of the array.

Described below is how to prepare an array of immobilized first strands, how to prepare and/or design a primer useful according to the invention, how to prime synthesis of a second strand that is complementary to- and duplexed with the first array-bound strand, how to incorporate a sequence specifying a recognition site within a nucleic acid sequence for a protein, and how to bind a protein thereto.

Nucleic acid arrays of the invention are prepared as described herein below in the section entitled "Bimolecular Double Stranded Nucleic Acid Arrays".

The nucleic acid array is prepared using nucleic acid sequences containing recognition sites within a nucleic acid sequence for a protein or proteins.

Proteins and Recognition Sequences Therefor Useful According to the Invention

A recognition site within a nucleic acid sequence for a protein useful according to the invention may be based on a naturally-occurring DNA sequence or synthetic (modified) version of such a sequence which is of higher or lower affinity for a given protein than is a corresponding natural sequence. Recognition sites within a nucleic acid sequence for a protein useful according to the invention include, but are not limited to, the following *E. coli* recognition sites within a nucleic acid sequence for proteins which bind DNA:

| Gene Encoding Protein | Recognition Site for a Protein (Uppercase = base most frequently observed at that position) | |
|---|---|---|
| FadR | ATCTGGTACGACCAGAT | [SEQ ID NO: 3] |
| Ada | AAAGCGCA | |
| Crp | aaaTGTGAtct agaTCACAttt | [SEQ ID NO: 4] |
| HsdM | AAC(n$_6$)GTGC | [SEQ ID NO: 5] |
| HsdR | AAC(n$_6$)GTGC | [SEQ ID NO: 5] |
| CI_434 | ACAAtat ataTTGT | [SEQ ID NO: 6] |

-continued

| Gene Encoding Protein | Recognition Site for a Protein (Uppercase = base most frequently observed at that position) | |
|---|---|---|
| Cro_434 | ACAAtat ataTTGT | [SEQ ID NO: 6] |
| TrpR | ACTAgtt | |
| Lrp | AgaATw n wATtcT | [SEQ ID NO: 7] |
| MetJ | AGACGTCT | |
| MalI | ATAAAac gtTTTAT | [SEQ ID NO: 8] |
| Fnr | aTTGATnn nnATCAAt | [SEQ ID NO: 9] |
| OxyR | ATyG($n_6$)CrAT | [SEQ ID NO: 10] |
| RpoH32 | ccccc($n_{18}$)cccc | [SEQ ID NO: 11] |
| RafR | cCGAAAc gTTTCGg | [SEQ ID NO: 12] |
| Dcm | CCWGG | |
| NhaR | cgcartattcaygytgrtgat | [SEQ ID NO: 13] |
| RpoN54 | ctggc ($n_7$) ttgca | [SEQ ID NO: 14] |
| PhoB | CTkTCATAwAwCTGTCAy | [SEQ ID NO: 15] |
| Fur | GAAAATAATTCTTATTTCG | [SEQ ID NO: 16] |
| Dam | GATC | |
| DnaB | GATCTnTTnTTTT | [SEQ ID NO: 17] |
| SoxS | GCAC($n_7$)CAA | [SEQ ID NO: 18] |
| MalT | GGAKGA | |
| GalR | gTGTAAnc gnTTACAc | [SEQ ID NO: 19] |
| RpoS38 | gttaag($n_{18}$)cgtcc | [SEQ ID NO: 20] |
| LexA | taCTGTatat atatACAGta | [SEQ ID NO: 21] |
| EbgR | tAGTAAaa n ttTTACTa | [SEQ ID NO: 22] |
| CI_lam | tATCACcg n gcGTGATa | [SEQ ID NO: 23] |
| Cro_lam | tATCACcg n gcGTGATa | [SEQ ID NO: 23] |
| HipB | TATCC($N_8$)GGATA | [SEQ ID NO: 24] |
| MetR | TGAA ($n_5$) TTCA | [SEQ ID NO: 25] |
| FruR | TGAAAC GTTTCA | [SEQ ID NO: 26] |
| ArgR | tGAATan ntATTCa | [SEQ ID NO: 27] |
| NtrC | TGCACCww n ww GGTGCA | [SEQ ID NO: 28] |
| TyrR | TGTAAA($N_6$)TTTACA | [SEQ ID NO: 29] |
| DicA | TGTTAnGyyA TrrCnTAACA | [SEQ ID NO: 30] |
| DicC | TGTTAnGyyA TrrCnTAACA | [SEQ ID NO: 30] |
| AraC | TnTGGAC($n_6$)GCTA | [SEQ ID NO: 31] |
| DnaA | TTATCCACA | |
| RpoD70 | ttgaca($n_{16-18}$)tataat | [SEQ ID NO: 32, 33 and 34] |
| CytR | tTGAwCn nGwTCAt | [SEQ ID NO: 35] |
| IlvY | TTGC ($n_6$) GCAA | [SEQ ID NO: 36] |
| C2_lam | TTGC($n_6$)TTGC | [SEQ ID NO: 37] |
| LacI | tTGTGAgc($n_{0-1}$)gcTCACAa | [SEQ ID NO: 38 and 39] |
| DeoR | tTGTTAgaa ttcTAACAa | [SEQ ID NO: 40] |
| KorB | TTTAGC n GCTAAA | [SEQ ID NO: 41] |
| HimA | WATCAANNNNTTR | [SEQ ID NO: 42] |
| GlpR | wATGTTCGwT AwCGAACATw | [SEQ ID NO: 43] |

Nucleic Acid/Protein Array Assays

Assays according to the invention include incubation of a nucleic acid array (produced as described below) with a protein, wherein the nucleic acid member molecules of the array comprise at least two recognition sites for a protein, such that a recognition site for a protein of a first member of the array is different from a recognition site for a protein of a second member of the array. The buffer used in the assay is generally a physiological buffer which does not result in denaturation of the protein; for example, a no-salt or low-salt buffer at neutral pH. Such a buffer might include 0–1M salt, 1–100 mM Tris-HCl, pH 8.0. The protein may be present in the buffer in the subpicomolar-to-millimolar range, for example, in the micromolar-to-nanomolar range. The incubation is performed at about physiological temperature for those proteins that are active at this temperature, or may be performed at low temperature (0° C.) using, for example, frost-tolerant proteins of certain plants, or at very high temperatures (even up to 100° C.) using thermophilic proteins.

Double-Stranded Bimolecular Nucleic Acid Arrays

I. Preparation of an Array of Immobilized First Nucleic Acid Strands

Synthesis of a nucleic acid array useful according to the present invention is a bipartite process, which entails the production of a diverse array of single-stranded nucleic acid molecules that are immobilized on the surface of a solid support matrix, followed by priming and enzymatic synthesis of a second nucleic acid strand, comprising either RNA or DNA. A highly preferred method of carrying out synthesis of the immobilized single-stranded array is that of Lockhart, described in U.S. Pat. No. 5,556,752 the contents of which are herein incorporated by reference. Of the methods described therein, that which is of particular use describes the synthesis of such an array on the surface of a single solid support having a plurality of preselected regions. A method whereby each chemically-distinct feature of the array is synthesized on a separate solid support is also described by Lockhart. These methods, and others, are briefly summarized below.

The solid support may comprise biological, nonbiological, organic or inorganic materials, or a combination of any of these. It is contemplated that such materials may exist as particles, strands, precipitates, gels, sheets, tubing, spheres, containers, capillaries, pads, slices, films, plates or slides. Preferably the solid support takes the form of plates or slides, small beads, pellets, disks or other convenient forms. It is highly preferred that at least one surface of the support is substantially flat. The solid support may take on alternative surface configurations. For example, the solid support may contain raised or depressed regions on which synthesis takes place. In some instances, the solid support will be chosen to provide appropriate light-absorbing characteristics. For example, the support may be a polymerized Langmuir Blodgett film, functionalized glass, Si, Ge, GaAs, GaP, $SiO_2$, $SiN_4$, modified silicon, or one of a variety of gels or polymers such as (poly) tetrafluoroethylene, (poly)vinylidendifluoride, polystyrene, polycarbonate, or combinations thereof. Other suitable solid support materials may be used, and will be readily apparent to those of skill in the art. Preferably, the surface of the solid support will contain reactive groups, which could be carboxyl, amino, hydroxyl, thiol, or the like. More preferably, the surface will be optically transparent and will have surface Si—OH functionalities, such as are found on silica surfaces.

According to the invention, a first nucleic acid strand is anchored to the solid support by as little as an intermolecular covalent bond. Alternatively, a more elaborate linking molecule may attach the nucleic acid strand to the support. Such a molecular tether may comprise a surface-attaching portion which is directly attached to the solid support. This portion can be bound to the solid support via carbon-carbon bonds using, for example, supports having (poly) trifluorochloroethylene surfaces, or preferably, by siloxane bonds (using, for example, glass or silicon oxide as the solid support). Siloxane bonds with the surface of the support can be formed via reactions of surface attaching portions bearing trichlorosilyl or trialkoxysilyl groups. The surface attaching groups will also have a site for attachment of the longer chain portion. It is contemplated that suitable attachment groups may include amines, hydroxyl, thiol, and carboxyl groups. Preferred surface attaching portions include aminoalkylsilanes and hydroxyalkylsilanes. It is particularly preferred that the surface attaching portion of the spacer is selected from the group comprising bis(2-hydroxyethyl)-aminopropyltriethoxysilane, 2-hydroxyethylaminopropyltriethoxysilane, aminopropyltriethoxysilane and hydroxypropyltriethoxysilane.

The longer chain portion of the spacer can be one of a variety of molecules which are inert to the subsequent conditions for polymer synthesis, examples of which include: aryl acetylene, ethylene glycol oligomers containing 2–14 monomer units, diamines, diacids, amino acids, peptides, or combinations thereof. It is contemplated that the longer chain portion is a polynucleotide. The longer chain portion which is to be used as part of the spacer can be selected based upon its hydrophilic/hydrophobic properties to improve presentation of the double-stranded oligonucleotides to certain receptors, proteins or drugs. It can be constructed of polyethyleneglycols, polynucleotides, alkylene, polyalcohol, polyester, polyamine, polyphosphodiester and combinations thereof.

Additionally, for use in synthesis of the arrays of the invention, the spacer will typically have a protecting group, attached to a functional group (i.e., hydroxyl, amino or carboxylic acid) on the distal or terminal end of the chain portion (opposite the solid support). After deprotection and coupling, the distal end is covalently bound to an oligomer.

As used in discussion of the spacer region, the term "alkyl" refers to a saturated hydrocarbon radical which may be straight -chain or branced-chain (for example, ethyl, isopropyl, t-amyl, or 2,5-0dimethylhexyl). When "alkyl" or "alkylene" is used to refer to a linking group or a spacer, it is taken to be a group having two available valences for covalent attachment, for example, $-CH_2CH_2-$, $-CH_2CH_2CH_2-$, $-CH_2CH_2CH(CH_3)CH_2--CH_2(CH_2CH_2)_2CH_2-$.

Preferred alkyl groups as substitutents are those containing 1 to 10 carbon atoms, with those containing 1 ato 6 carbon atoms being particularly preferred. Preferred alkyl or alkylene groups as linking groups are those containing 1 to 20 carbon atoms, with those containing 3 to 6 carbon atoms being particularly preferred. The term "polyethylene glycol" is used to refer to those molecules which have repeating units of ethylene glycol, for example, hexaethylene glycol $(HO-(CH_2CH_2O)_5-CH_2(CH_2CH_2OH))$. When the term "polyethylene glycol" is used to refer to linking groups and spacer groups, it would be understood by one of skill in the art that other polyethers of polyols could be used as well (i.e., polypropylene glycol or mistures of ethylene and propeylene glycols).

The term "protecting group", as used herein, refers to any of the groups which are designed to block one reactive site in a molecule while a chemical reaction is carried out at another reactive site. More particularly, the protecting groups used herein can be any of those groups described in Greene et al., 1991, *Protective In Organic Chemistry*, 2nd Ed., John Wiley & Sons, New York, N.Y., incorporated herein by reference. The proper selection of protecting groups for a particular synthesis will be governed by the overall methods employed in the synthesis. For example, in "light-directed" synthesis, discussed below, the protecting groups will be photolabile protecting groups, e.g. NVOC and MeNPOC. In other methods, protecting groups may be removed by chemical methods and include groups such as FMOC, DMT and others known to those of skill in the art.

a. Nucleic Acid Arrays on a Single Support

1. Light-directed Methods

Where a single solid support is employed, the oligonucleotides of the present invention can be formed using a variety of techniques known to those skilled in the art of polymer synthesis on solid supports. For example, "light-directed" methods, techniques in a family of methods known as VLSIPS™ methods, are described in U.S. Pat. No. 5,143,854 and U.S. Pat. No. 5,510,270 and U.S. Pat. No. 5,527,681, which are herein incorporated by reference. These methods, which are illustrated in FIG. 1 (adapted from Pease et al., 1994, *Proc. Natl. Acad. Sci. U.S.A.*, 91: 5022–5026), involve activating predefined regions of a solid support and then contacting the support with a preselected monomer solution. These regions can be activated with a light source, typically shown through a mask (much in the manner of photolithography techniques used in integrated circuit fabrication). Other regions of the support remain inactive because illumination is blocked by the mask and they remain chemically protected. Thus, a light pattern defines which regions of the support react with a given monomer. By repeatedly activating different sets of predefined regions and contacting different monomer solutions with the support, a diverse array of polymers is produced on the support. Other steps, such as washing unreacted monomer solution from the support, can be used as necessary. Other applicable methods include mechanical techniques such as those described in PCT No. 92/10183, U.S. Pat. No. 5,384,261 also incorporated herein by reference for all purposes. Still further techniques include bead based techniques such as those described in PCT US/93/04145, also incorporated herein by reference, and pin based methods such as those described in U.S. Pat. No. 5,288,514, also incorporated herein by reference.

The VLSIPS™ methods are preferred for making the compounds and arrays of the present invention. The surface of a solid support, optionally modified with spacers having photolabile protecting groups such as NVOC and MeNPOC, is illuminated through a photolithographic mask, yielding reactive groups (typically hydroxyl groups) in the illuminated regions. A 3'-O-phosphoramidite activated deoxynucleoside (protected at the 5'-hydroxyl with a photolabile protecting group) is then presented to the surface and chemical coupling occurs at sites that were exposed to light. Following capping and oxidation, the support is rinsed and the surface illuminated through a second mask, to expose additional hydroxyl groups for coupling. A second 5'-protected, 3'-O-phosphoramidite activated deoxynucleoside is presented to the surface. The selective photodeprotection and coupling cycles are repeated until the desired set of oligonucleotides is produced. Alternatively, an oligomer of from, for example, 4 to 30 nucleotides can be added to each of the preselected regions rather than synthesize each member one nucleotide monomer at a time.

2. Flow Channel or Spotting Methods

Additional methods applicable to array synthesis on a single support are described in U.S. Pat. No. 5,384,261, incorporated herein by reference for all purposes. In the methods disclosed in these applications, reagents are delivered to the support by either (1) flowing within a channel defined on predefined regions or (2) "spotting" on predefined regions. Other approaches, as well as combinations of spotting and flowing, may be employed as well. In each instance, certain activated regions of the support are mechanically separated from other regions when the monomer solutions are delivered to the various reaction sites.

A typical "flow channel" method applied to arrays of the present invention can generally be described as follows: Diverse polymer sequences are synthesized at selected regions of a solid support by forming flow channels on a surface of the support through which appropriate reagents flow or in which appropriate reagents are placed. For example, assume a monomer "A" is to be bound to the support in a first group of selected regions. If necessary, all or part of the surface of the support in all or a part of the selected regions is activated for binding by, for example, flowing appropriate reagents through all or some of the channels, or by washing the entire support with appropriate reagents. After placement of a channel block on the surface of the support, a reagent having the monomer A flows through or is placed in all or some of the channel(s). The channels provide fluid contact to the first selected regions, thereby binding the monomer A to the support directly or indirectly (via a spacer) in the first selected regions.

Thereafter, a monomer B is coupled to second selected regions, some of which may be included among the first selected regions. The second selected regions will be in fluid contact with a second flow channel(s) through translation, rotation, or replacement of the channel block on the surface of the support; through opening or closing a selected valve; or through deposition of a layer of chemical or photoresist. If necessary, a step is performed for activating at least the second regions. Thereafter, the monomer B is flowed through or placed in the second flow channel(s), binding monomer B at the second selected locations. In this particular example, the resulting sequences bound to the support at this stage of processing will be, for example, A, B, and AB. The process is repeated to form a vast array of sequences of desired length at known locations on the support.

After the support is activated, monomer A can be flowed through some of the channels, monomer B can be flowed through other channels, a monomer C can be flowed through still other channels, etc. In this manner, many or all of the reaction regions are reacted with a monomer before the channel block must be moved or the support must be washed and/or reactivated. By making use of many or all of the available reaction regions simultaneously, the number of washing and activation steps can be minimized.

One of skill in the art will recognize that there are alternative methods of forming channels or otherwise protecting a portion of the surface of the support. For example, a protective coating such as a hydrophilic or hydrophobic coating (depending upon the nature of the solvent) is utilized over portions of the support to be protected, sometimes in combination with materials that facilitate wetting by the reactant solution in other regions. In this manner, the flowing solutions are further prevented from passing outside of their designated flow paths.

The "spotting" methods of preparing compounds and arrays of the present invention can be implemented in much the same manner. A first monomer, A, can be delivered to and coupled with a first group of reaction regions which have been appropriately activated. Thereafter, a second monomer, B, can be delivered to and reacted with a second group of activated reaction regions. Unlike the flow channel embodiments described above, reactants are delivered in relatively small quantities by directly depositing them in selected regions. In some steps, the entire support surface can be sprayed or otherwise coated with a solution, if it is more efficient to do so. Precisely measured aliquots of monomer solutions may be deposited dropwise by a dispenser that moves from region to region. Typical dispensers include a micropipette to deliver the monomer solution to the support and a robotic system to control the position of the micropipette with respect to the support, or an ink-jet printer. In other embodiments, the dispenser includes a series of tubes, a manifold, an array of pipettes, or the like so that various reagents can be delivered to the reaction regions simultaneously.

3. Pin-Based Methods

Another method which is useful for the preparation of the immobilized arrays of single-stranded DNA molecules X of the present invention involves "pin-based synthesis." This method, which is described in detail in U.S. Pat. No. 5,288,514, previously incorporated herein by reference, utilizes a support having a plurality of pins or other extensions. The pins are each inserted simultaneously into individual reagent containers in a tray. An array of 96 pins is commonly utilized with a 96-container tray, such as a 96-well microtitre dish.

Each tray is filled with a particular reagent for coupling in a particular chemical reaction on an individual pin. Accordingly, the trays will often contain different reagents. Since the chemical reactions have been optimized such that each of the reactions can be performed under a relatively similar set of reaction conditions, it becomes possible to conduct multiple chemical coupling steps simultaneously. The invention provides for the use of support(s) on which the chemical coupling steps are conducted. The support is optionally provided with a spacer, S, having active sites. In the particular case of oligonucleotides, for example, the spacer may be selected from a wide variety of molecules which can be used in organic environments associated with synthesis as well as aqueous environments associated with binding studies such as may be conducted between the nucleic acid members of the array and other molecules. These molecules include, but are not limited to, proteins (or fragments thereof), lipids, carbohydrates, proteoglycans and nucleic acid molecules. Examples of suitable spacers are polyethyleneglycols, dicarboxylic acids, polyamines and alkylenes, substituted with, for example, methoxy and ethoxy groups. Additionally, the spacers will have an active site on the distal end. The active sites are optionally protected initially by protecting groups. Among a wide variety of protecting groups which are useful are FMOC, BOC, t-butyl esters, t-butyl ethers, and the like.

Various exemplary protecting groups are described in, for example, Atherton et al., 1989, *Solid Phase Peptide Synthesis*, IRL Press, incorporated herein by reference. In some embodiments, the spacer may provide for a cleavable function by way of, for example, exposure to acid or base.

b. Arrays on Multiple Supports

Yet another method which is useful for synthesis of compounds and arrays of the present invention involves "bead based synthesis." A general approach for bead based synthesis is described in PCT/US93/04145 (filed Apr. 28, 1993), the disclosure of which is incorporated herein by reference.

For the synthesis of molecules such as oligonucleotides on beads, a large plurality of beads are suspended in a suitable carrier (such as water) in a container. The beads are provided with optional spacer molecules having an active site to which is complexed, optionally, a protecting group.

At each step of the synthesis, the beads are divided for coupling into a plurality of containers. After the nascent oligonucleotide chains are deprotected, a different monomer solution is added to each container, so that on all beads in a given container, the same nucleotide addition reaction occurs. The beads are then washed of excess reagents, pooled in a single container, mixed and re-distributed into another plurality of containers in preparation for the next round of synthesis. It should be noted that by virtue of the large number of beads utilized at the outset, there will similarly be a large number of beads randomly dispersed in the container, each having a unique oligonucleotide sequence synthesized on a surface thereof after numerous rounds of randomized addition of bases. As pointed out by Lockhart (U.S. Pat. No. 5,556,752) an individual bead may be tagged with a sequence which is unique to the double-stranded oligonucleotide thereon, to allow for identification during use.

II. Preparation of Oligonucleotide Primers

Oligonucleotide primers useful to synthesize bimolecular arrays are single-stranded DNA or RNA molecules that are hybridizable to a nucleic acid template to prime enzymatic synthesis of a second nucleic acid strand. The primer may therefore be of any sequence composition or length, provided it is complementary to a portion of the first strand.

It is contemplated that such a molecule is prepared by synthetic methods, either chemical or enzymatic. Alternatively, such a molecule or a fragment thereof may be naturally occurring, and may be isolated from its natural source or purchased from a commercial supplier. It is contemplated that oligonucleotide primers employed in the present invention will be 6 to 100 nucleotides in length, preferably from 10 to 30 nucleotides, although oligonucleotides of different length may be appropriate.

Additional considerations with respect to design of a selected primer relate to duplex formation, and are described in detail in the following section.

III. Primed Enzymatic Second-Strand Nucleic Acid Synthesis to form a Double-Stranded Array Of central importance in carrying out preparation of a bimolecular array is selective hybridization of an oligonucleotide primer to the first nucleic acid strand in order to permit enzymatic synthesis of the second nucleic acid strand. Any of a number of enzymes well known in the art can be utilized in the synthesis reaction. Preferably, enzymatic synthesis of the second strand is performed using an enzyme selected from the group comprising DNA polymerase I (exo$^{(-)}$ Klenow fragment), T4 DNA polymerase, T7 DNA polymerase, modified T7 DNA polymerase, Taq DNA polymerase, exo$^{(-)}$ vent DNA polymerase, exo$^{(-)}$ deep vent DNA polymerase, reverse transcriptase and RNA polymerase.

Typically, selective hybridization will occur when two nucleic acid sequences are substantially complementary (typically, at least about 65% complementary over a stretch of at least 14 to 25 nucleotides, preferably at least about 75%, more preferably at least about 90% complementary). See Kanehisa, M., 1984, *Nucleic Acids Res.* 12: 203, incorporated herein by reference. As a result, it is expected that a certain degree of mismatch at the priming site can be tolerated. Such mismatch may be small, such as a mono-, di- or tri-nucleotide. Alternatively, it may encompass loops, which we define as regions in which mismatch encompasses an uninterrupted series of four or more nucleotides. Note that such loops within the oligonucleotide priming site are encompassed by the present invention; however, the invention does not provide double-stranded nucleic acids that comprise loop structures between the 5' end of the first strand and the 3' end of the second strand. In addition, loop structures outside the priming site, but which do not encumber the 5' end of the first strand or the 3' end of the second strand are not provided by the present invention, since there is no known mechanism for generating such structures in the course of enzymatic second-strand nucleic acid synthesis. Both the 5' end of the first strand and the 3' end of the second strand must be free of attachment to each other via a continuous single strand.

Either strand may comprise RNA or DNA. Overall, five factors influence the efficiency and selectivity of hybridization of the primer to the immobilized first strand. These factors are (i) primer length, (ii) the nucleotide sequence and/or composition, (iii) hybridization temperature, (iv) buffer chemistry and (v) the potential for steric hindrance in the region to which the probe is required to hybridize.

There is a positive correlation between primer length and both the efficiency and accuracy with which a primer will anneal to a target sequence; longer sequences have a higher $T_M$ than do shorter ones, and are less likely to be repeated within a given first nucleic acid strand, thereby cutting down on promiscuous hybridization. Primer sequences with a high G-C content or that comprise palindromic sequences tend to self-hybridize, as do their intended target sites, since unimolecular, rather than bimolecular, hybridization kinetics are genererally favored in solution; at the same time, it is important to design a primer containing sufficient numbers of G-C nucleotide pairings to bind the target sequence tightly, since each such pair is bound by three hydrogen bonds, rather than the two that are found when A and T bases pair. Hybridization temperature varies inversely with primer annealing efficiency, as does the concentration of organic solvents, e.g. formamide, that might be included in a hybridization mixture, while increases in salt concentration facilitate binding. Under stringent hybridization conditions, longer probes must be used, while shorter ones will suffice under more permissive conditions. Stringent hybridization conditions will typically include salt concentrations of less than about 1M, more usually less than about 500 mM and preferably less than about 200 mM. Hybridization temperatures can be as low as 5° C., but are typically greater than 22° C., more typically greater than about 30° C., and preferably in excess of about 37° C. Longer fragments may require higher hybridization temperatures for specific hybridization. As several factors may affect the stringency of hybridization, the combination of parameters is more important than the absolute measure of any one alone.

Primers must be designed with the above first four considerations in mind. While estimates of the relative merits of numerous sequences can be made mentally, computer programs have been designed to assist in the evaluation of these several parameters and the optimization of primer sequences. Examples of such programs are "PrimerSelect" of the DNAStar™ software package (DNAStar, Inc.; Madison, Wis.) and OLIGO 4.0 (National Biosciences, Inc.). Once designed, suitable oligonucleotides may be prepared by the phosphoramidite method described by Beaucage and Carruthers, 1981, *Tetrahedron. Lett.*, 22: 1859–1862, or by the triester method according to Matteucci et al., 1981, *J. Am. Chem. Soc.*, 103: 3185, both incorporated herein by reference, or by other chemical methods using either a commercial automated oligonucleotide synthesizer or VLSIPS™ technology (discussed in detail below).

The fifth consideration, steric hindrance, is one that was of particular relevance to the development of the invention disclosed herein. While methods for the primed, enzymatic synthesis of second nucleic acid strands from immobilized first strands are known in the art (see Uhlen, U.S. Pat. No. 5,405,746 and Utermohlen, U.S. Pat. No. 5,437,976), the present method differs in that the priming site, as determined by the location of the 3' end of the first strand (X), is adjacent to the surface of the solid support. In a typical silica-based chip array, made as per Lockhart (U.S. Pat. No. 5,556,752), a 20 $\mu m^2$ region carries approximates $4 \times 10^6$ functional copies of a specific sequence, with an intermolecular spacing distance of about 100 Å (Chee et al., 1996, *Science*, 274: 610–614). As a result, it is necessary that the oligonucleotide primer hybridize efficiently to an anchored target in a confined space, and that synthesis proceed outward from the support. In the above-referenced disclosures, it is the 5' end of the first oligonucleotide strand which is linked to the matrix; therefore, priming of the free end of that molecule is permitted, and second-strand extension proceeds toward the solid support. Under the circumstances, significant uncertainty existed as to whether oligonucleotide priming of the end of the first strand proximal to the solid support would occur at a sufficiently high frequency to yield a high-density double-stranded nucleic acid array.

EXAMPLE 1

This example illustrates the general synthesis of an array of bimolecular, double-stranded oligonucleotides on a solid support which arrays, such as may comprise recognition sites for a protein or proteins.

As a first step, single-stranded DNA molecules were synthesized on a solid support using standard light-directed methods (VLSIPST™ protocols), as as described above, using the method of Lockhart, U.S. Patent No. 5,556,752, the contents of which incoporated above by reference.

Figure 2:
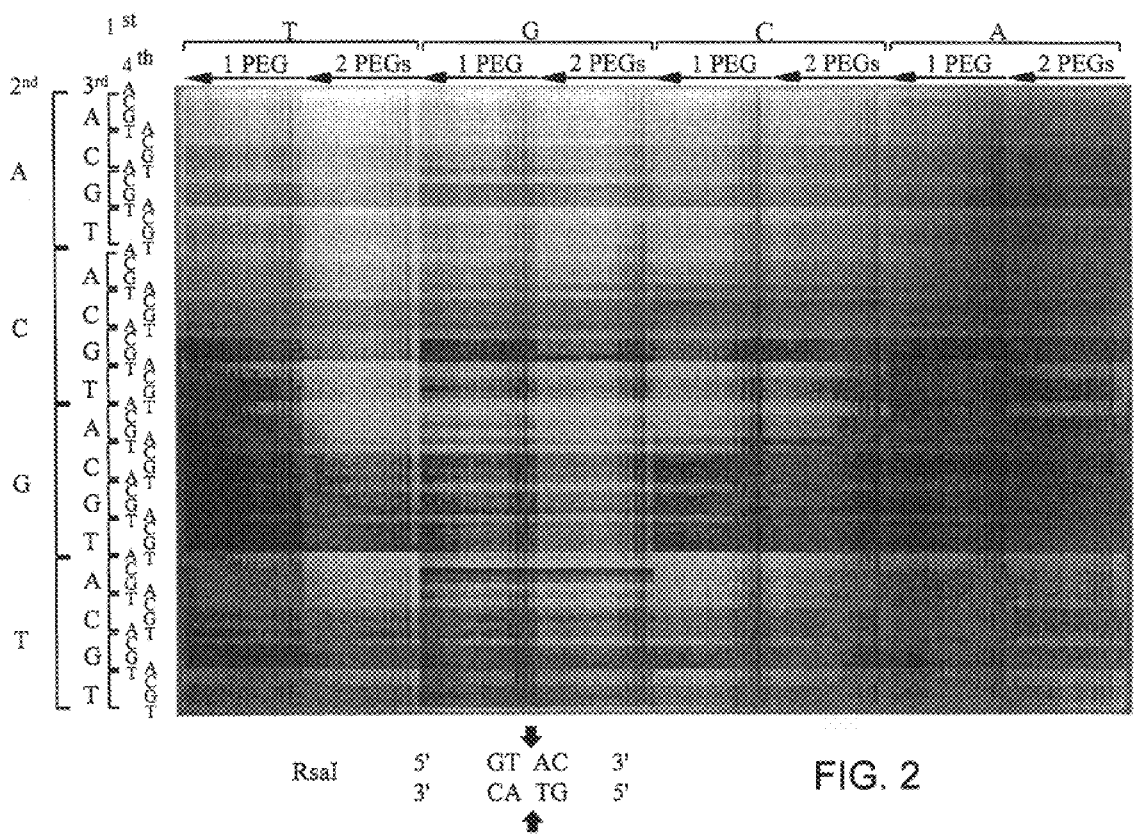
FIG. 2 presents a photomicrograph of a fluorescently-labeled array of bimolecular, double-stranded DNA molecules on a silica chip.

Hexaethylene glycol (PEG) linkers were used to covalently attach the synthesized oligonucleotides to the derivatized glass surface. A heterogeneous array of linkers was formed such that some sectors of the silica chip had linkers comprising two PEG linkers, while other sectors bore linkers comprising a single PEG molecule (FIG. 2). In addition, the intermolecular distance between linker molecules (and, consequently, nascent nucleic acid strands) was varied such that for either length of linker and for each of the 9,600 distinct molecular species synthesized, were 15 different chip sectors representing the following range of strand densities. These densities, expressed as the percent of total anchoring sites occupied by nucleic acid molecules, are shown in Table 1.

TABLE 1

| % of sites filled |
| --- |
| 0.4 |
| 1.6 |
| 3.1 |
| 6.2 |
| 12.5 |
| 25.0 |
| 31.5 |
| 39.7 |
| 50.0 |
| 63.0 |
| 69.1 |
| 75.8 |
| 83.1 |
| 91.2 |
| 100.0 |

Synthesis of the first strand proceeded one nucleotide at a time using repeated cycles of photo-deprotection and chemical coupling of protected nucleotides. The nucleotides each had a protecting group on the base portion of the monomer as well as a photolabile MeNPoc protecting group on the 5' hydroxyl. Note that each of the different molecular species occupies a different physical region on the chip so that there is a one-to-one correspondence between molecular identity and physical location. Moving outward from the chip, the sequence of each molecule proceeds from its 3' to its 5' end (the 3' end of the DNA molecule is attached to the solid surface via a silyl group and 2 PEG linkers), as is the case when chemical synthetic methods are utilized.

Second strand synthesis, as stated above, requires priming of a site at the 3' end of the first nucleic acid strand, followed by enzymatic extension of the primed sequence. DNA polymerase I (exo$^{(-)}$ Kienow fragment) was employed in this experiment, although numerous other enzymes, as discussed above, may be employed advantageously. This particular enzyme is optimally active at 37° C.; therefore, two priming sites and the corresponding complementary primers were designed that were predicted to bind efficiently and yet exhibit a minimum of secondary structure at that temperature according to calculations performed by the DNAStar "PrimerSelect" computer program, which was employed for this purpose. The sequences of these primers were as follows:

1s 5'-TCCACACTCTCCAACA-3' [SEQ ID NO: 1] (estimated $T_M$=36.8° C.)

2s 5'-GGACCCTTTGACTTGA-3' [SEQ ID NO: 2] (estimated $T_M$=38.7° C.)

Note that the optimal reaction temperature varies considerably among polymerases. Also of use according to the methods of the invention are exo$^{(-)}$ vent DNA polymerase and exo$^{(-)}$ deep vent DNA polymerase (both commercially available from New England Biolabs, Beverly, Mass.), which are optimally active at 72° C. and approximately 30% active at 50° C., according to the manufacturer. Were these enzymes used instead, longer primer sequences, or those with a higher G-C content, would have to have been employed.

In the case of the synthesis presented in FIG. 2, primer S1 [SEQ ID NO: 1] was used. The reaction conditions were as follows:

Prehybridization of chip: 0.005% Triton X-100, 0.2 mg/ml acetylated bovine serum albumin (BSA), 10 mM Tris-HCl (pH 7.5), 5 mM $MgCl_2$ and 7.5 mM dithiothreitol (DTT) at 37° C. for 30 to 60 minutes on a rotisserie.

Second-strand primer extension and fluorescein labeling: 0.005% Triton, 10 mM Tris-HCl (pH 7.5), 5 mM $MgCl_2$, 7.5 mM DTT, 0.4 mM dNTP's, 0.4 µM primer, 0.04 U/µl DNA Polymerase I (3' to 5' exo$^{(-)}$ Klenow fragment, New England Biolabs, Beverly, Mass.) and 0.0004 mM of fluorescein-12-labeled dATP at 37° C. for 1 to 2 hours on a rotisserie, followed by a wash in 0.005% Triton X-100 in 6×SSPE at room temperature. (Note that an alternate labeling procedure, not used in the experiment presented in this Example, is one in which unlabeled extension is performed, followed by labeled primer extension using terminal deoxynucleotide transferase. This reaction takes place as follows: 0.005% Triton X-100, 10 mM Tris acetate, pH 7.5, 10 mM magnesium acetate, 50 mM potassium acetate, 0.044 U/µl terminal transferase and 0.014 mM of any fluorescein-12-labeled dideoxynucleotide at 37° C. for 1–2 hr. on a rotisserie, followed by a wash in 0.005% Triton X-100 in 6×SSPE at room temperature.)

Figure 3:
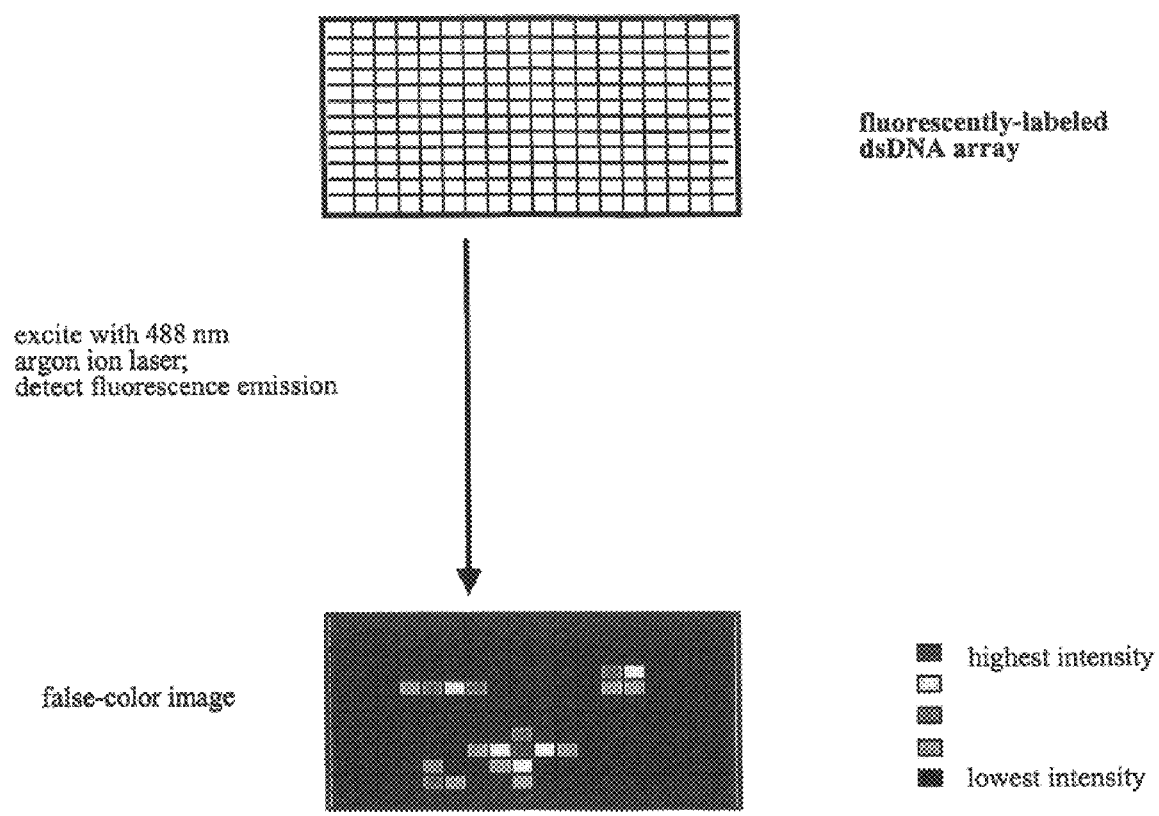
FIG. 3 presents confocal argon laser scanning to detect fluorescently-labeled, surface-bound nucleic acid molecules.

To confirm that second-strand synthesis had taken place, the chip was scanned under a layer of wash buffer for fluorescence in an argon laser confocal scanner (see U.S. Pat. No. 5,578,832). This device exposes the molecules of the array to irradiation at a wavelength of 488 nanometers, which excites electrons in the fluorescein moiety, resulting in fluorescent emissions, which are then recorded at each position of the chip (FIG. 3). Since the first strand was unlabeled, the efficiency of second-strand synthesis can be measured. The result is shown in FIG. 2, where various sectors of the chip fluoresce with different intensities, in proportion both to strand density and to the proportion of dATP residues in the second strand.

Figure 4:
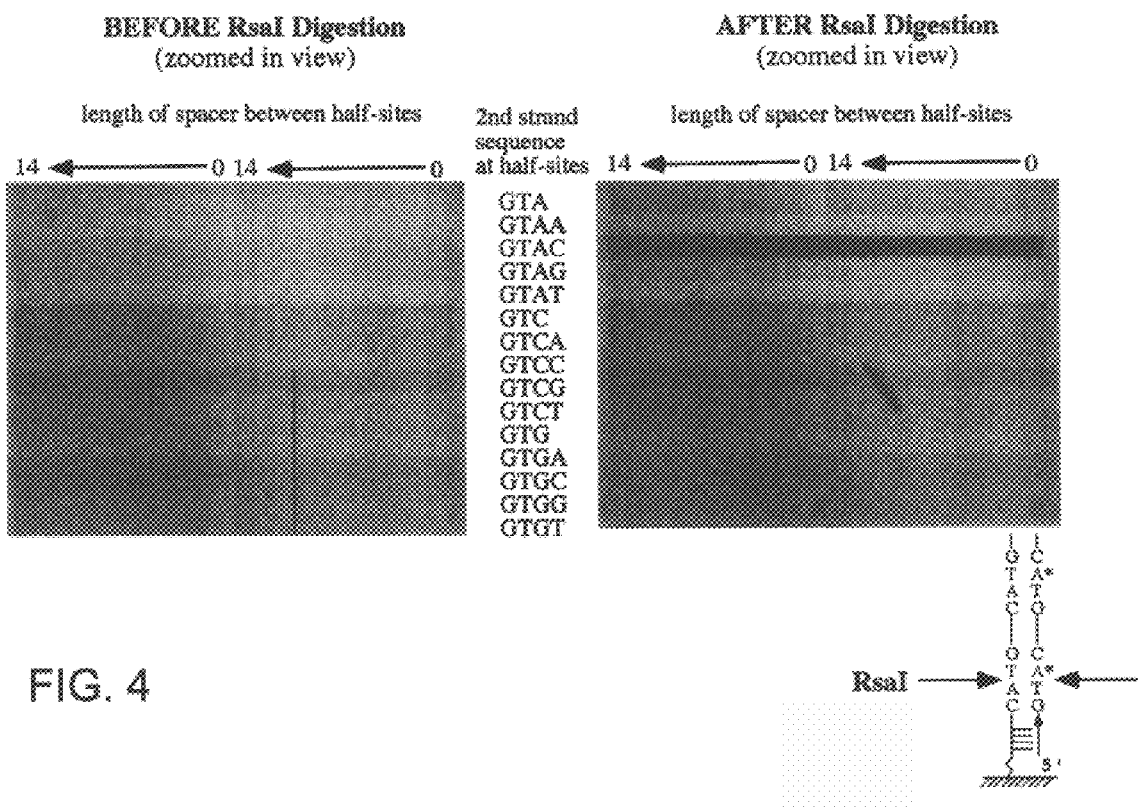
FIG. 4 presents RsaI digestion of a fluorescently-labeled array of bimolecular, double-stranded DNA molecules on a silica chip.

Further confirmation of successful second-strand synthesis was gained from a biochemical assay of the chip. According to the first-strand synthesis procedure, several sectors of the chip were designed such that the several unique sequences synthesized at those positions contained a 4 base motif which, when double-stranded, would form a recognition site for the endonuclease RsaI. The chip was digested in RsaI, using the manufacturer's recommended incubation conditions. Upon re-scanning of the chip in the argon laser scanner, a dark area appeared. This can be seen in FIG. 2, and is shown in detail in FIG. 4. Since the ability of the enzyme to cleave the sequence from the chip is dependent upon the sequence being double-stranded, synthesis, at least to the point of the RsaI recognition site, must have occurred.

In addition to providing evidence of successful second-strand synthesis, cleavage of double-stranded nucleic acid molecules from the solid support with RsaI demonstrates that members of the array are accessible to proteins in solution, a requirement if the arrays of the invention are to be useful in carrying out assays of protein/DNA interactions.

EXAMPLE 2

Isolation of Proteins Which Bind a Candidate Recognition Site for a Protein of an Array An array of double-stranded nucleic acid molecules is made as described in Example 1, comprising test nucleic acid sequences of unknown protein-binding characteristics that are a) chosen because comparative sequence analysis or functional studies of a gene promoter implicates them as gene regulatory elements or b) generated de novo for use according to the invention. Alternatively, nucleic acid sequences that have been found to bind at least one known protein are used (see Example 3, below); a number of recognition sites for known proteins are listed above.

After nucleic acid synthesis, a sample comprising a plurality of protein molecules is incubated with the array under conditions under which permit protein:nucleic acid binding, as described above; such conditions may be relatively stringent (high salt—approximately 1M) or, if proteins are to be recovered which might bind recognition sites for a protein or proteins in vivo that are related (but not identical) to sequences comprised by features of the array, lower salt concentrations (0 to 100 mM) are used. Unbound protein molecules are then washed away. Bound proteins are eluted from the array using a high salt buffer, and transferred to a suitable storage buffer either through dialysis against- or precipitation and resuspension in such a buffer. Proteins are separated by any chromatographic procedure known in the art, e.g. two-dimensional gel electrophoresis, and then sequenced, also by standard methods, such as by mass spectrometry (e.g., liquid chromatography/electrospray ionization/ion trap tandem mass spectrometry) or Edman degradation.

Following identification of the bound proteins, their relative affinities for the recognition sites for a protein or proteins are, if desired, assayed singly by binding them to chips or chromatography supports to which are complexed oligonucleotides representing isolated sequences of the array and eluting them off in buffers of gradually increasing ionic strength; binding affinity is directly proportional to the salt concentration required to remove a given protein from a nucleic acid molecule. Alternatively, such binding affinities may be determined as described below in Example 7.

EXAMPLE 3

Assessment of Factors Which Influence Binding of a Protein to a Recognition Site for a Protein In addition to changes in salt concentration in an in vitro system (which do not normally reflect conditions which would occur in vivo), it is desirable to examine factors which might, in a living system, influence or be made to influence nucleic acid/protein interactions. This method is applicable if it is advantageous to inhibit binding of a protein to a particular recognition site for a protein in order to nullify its influence (appropriate or otherwise) on a given gene; alternatively, one might attempt to promote binding of such a protein to the cis-regulatory sequence of a gene for which the appropriate trans-regulatory factor is absent or defective. Such a procedure, in which the affinity of the phage λ 434 Cro protein for its cognate recognition site for a protein is examined, is described in this example.

A λ 434 Cro protein array is provided as follows:

In one embodiment of the invention, the DNA molecules referred to in Example 1 are synthesized so as to include the sequence ACAAtat ataTTGT [SEQ ID NO: 6], which specifies the recognition site for the λ 434 Cro protein.

λ 434 Cro protein is provided as described in the prior art, and is brought to a concentration of approximately 100 nM in 10 mM NaCl, 50 mM Tris-HCl, pH 8.0, and incubated on the nucleic acid array made according to the invention (as described above) for approximately 5 minutes at 37° C.

The λ 434 Cro nucleic acid/protein array is used according to the invention in several ways:

a) Binding affinities of other mutant Cro proteins, relative to λ 434 Cro, may be determined by binding labeled λ 434 Cro to the array in competition either with unlabeled λ 434 Cro (as a control) or the mutant test protein, also unlabeled. The degree to which each protein is able to prevent binding of labeled λ 434 Cro to the nucleic acid molecules of the array is indicative of its binding strength relative to that of λ 434 Cro, as judged by the amount of label which is detected on the array after unbound proteins are washed off. The amount of label present is inversely proportional to the affinity of the test protein for the recognition site for the λ 434 Cro protein.

b) The relative binding affinities of λ 434 Cro protein for mutant recognition sites for the λ 434 Cro protein are tested by incubating an array produced as above (wherein the λ 434 Cro protein molecules are, additionally, labeled) with double-stranded oligonucleotides comprising the mutant sites for λ 434 Cro protein. The amount of label present on the array is quantified both before incubation and after the oligonucleotides are washed away; the difference in label still attached to the array relative to a comparably-treated control in which no competitor or a non-specific competitor (such as poly dIdC or a population of random oligomers) is used is proportional to the affinity of λ 434 Cro protein for the mutant recognition sites for λ 434 Cro protein. Alternatively, both the labeled λ 434 Cro protein and the oligonucleotides are present together in a buffer in which a nucleic acid array produced as described above is incubated. A control incubation, containing no mutant oligonucleotides, is set up in parallel, and the amount of labeled protein bound to each is quantified.

c) Inhibitors of the binding interaction between λ 434 Cro protein and the recognition site for λ 434 Cro protein may be tested by either of the methods described in a) and b). Candidate inhibitors include substances which directly compete with λ 434 Cro for its recognition site or that compete with that recognition site for binding to λ 434 Cro protein, such as other proteins with higher affinity for the recognition site for λ 434 Cro protein than that of λ 434 Cro protein itself or nucleic acid molecules comprising engineered recognition sites for a protein for which λ 434 Cro protein may have higher affinity than it has for the native recognition site for λ 434 Cro protein. Inhibitors which indirectly prevent binding include proteins or other substances which may disrupt the proper dimerization of λ 434 Cro protein, such as salts, enzymes (e.g. proteases, kinases, phosphorylases, glycosylases) and other proteins with which it might form unproductive dimers (either because one subunit lacks affinity for a half-site of the recognition site for λ 434 Cro protein or because dimerization causes conformational changes in λ 434 Cro protein such that it is no longer functional)

EXAMPLE 4

Identification of Candidate Members of a Set of Co-regulated Genes Using Arrays of the Invention As in Example 2, an array of double-stranded nucleic acid molecules is made as described in Example 1, comprising test nucleic acid sequences of unknown protein-binding characteristics that are a) chosen because comparative sequence analysis or functional studies of a gene I 0 promoter implicates them as gene regulatory elements or b) generated de novo for use according to the invention. Alternatively, nucleic acid sequences that have been found to bind at least one known protein are used (see Example 3, above); recognition sites for a number of known proteins are listed above.

A protein complexed with a detectable label, such as a fluoresent tag or (as described below in Example 7) Green Fluorescent Protein, is incubated with the array under conditions which permit efficient protein/nucleic acid interactions, such as in a physiological salt buffer (also, above) at room temperature. After unbound protein is washed from the array, using physiological buffer minus protein as the wash solution, the array is scanned to detect the presence of label. The identities of recognition sites for a protein or proteins present on molecules of features of the array upon which label is detected are noted. Nucleic acid databases are searched with these sequences. Genes in whose regulatory regions such sequences appear, whether upstream or downstream of a gene, in introns, or in the 5' or 3' untranslated regions of its mature mRNA transcript, are classified as being potentially under the control of the test protein in vivo. If two or more of such genes are uncovered, they are said to form a set of candidate co-regulated genes, meaning that they may be under the control of one or more of the same trans-regulatory factors, resulting in a common expression profile, whether spatially or temporally. These genes may then undergo functional analysis by methods known in the art (e.g. expression studies, such as Northern analysis, of each in a normal genetic background as well as in one in which the test protein is mutated or absent) in order to confirm this supposition, if it is so desired.

EXAMPLES 5

Nucleic Acid/Protein Arrays Comprising Protein Heterodimers

While a number of proteins will bind recognition sites for a protein as monomers or as di-or multimeric units comprising a multiple copies of a single polypeptide sequence, others are able to bind only as heterogeneous aggregates, such as heterodimeric units. Recognition sites for a protein which are recognized by a heterodimer often lack the dyad symmetry of nucleic acid sequence which is relatively common among recognition sites for a protein to which protein homodimers bind. Typically, each monomer of a protein dimer (whether a homo- or heterodimer) binds what is termed a "half site". Given a protein which is known to bind a nucleic acid as part of a heterodimer and the sequence of the half site to which it binds, it is possible to determine the range of partners with which it might pair in order to bind a complete target sequence as follows:

An array of double-stranded nucleic acid molecules is prepared as described above, wherein at least a portion of features of the array comprise a recognition site for a protein wherein the half site recognized by the protein of interest (e.g., *E. coli* IHF) is fused to a random sequence, such that all oligonucleotide sequences of the chosen length (for example, all hexamers or octamers) are represented on the array in order to fill the remaining positions of the recognition sites for a protein or proteins on features thereof. The test protein is labeled by methods known in the art (radioactively, fluorescently, chemiluminescently, chromogenically or using mass-tags) and then incubated with the array in the presence of a pool of proteins comprising one or a plurality of potential binding partners under conditions which permit protein dimerization and protein/nucleic acid binding. After unbound protein is washed from the array, the array is scanned in order to detect bound label, as described above. Alternatively, an unlabeled test protein is used and, after removal of unbound protein from the array, an immunological detection scheme is employed, in which a primary antibody specific for the test protein is first applied, followed by a labeled secondary antibody specific for immunoglobulins of the host species in which the primary antibody was produced. Such labeled secondary antibodies are commercially available (for example, from Vector Laboratories; Burlingame, Calif.). Methods for the production of primary antibodies against a test protein, if such antibodies are not also commercially available, are well known in the art. The sequences to which label is bound are noted; these sequences (the half site to which the test protein binds in combination with the random half site to which a member of the protein pool binds) are then used individually to isolate each of the binding partners in sufficient quantities to permit protein sequencing. Oligonucleotides comprising the recognition sites for a protein on which label is dectected are bound to a chromatography matrix (such as cellulose) and placed in a column. A preparative amount (picomolar to millimolar concentrations in microliter to milliliter volumes) of the test protein is incubated with an aliquot of protein comparable to that used in binding the array (preferably, drawn from the same protein preparation) under identical buffer conditions, and the mixture is run over the column. After unbound protein is washed away, the bound complexes are washed from the column in a high salt buffer. The dissociated subunits are then separated chromatographically and the newly-isolated binding partner is sequenced, again by standard methods.

In order to determine whether the results gathered in vitro by according to the invention reflect a gene transcriptional mechanism that is found in vivo, it is necessary both to demonstrate that the test protein and a pairing partner isolated as described in this example are co-expressed (that is, expressed together both temporally and spatially in an organism)—if the two proteins do not co-exist in a cell, they cannot join to form a nucleic acid binding complex—and that the recognition site for a protein to which site the heteroduplex binds occurs in the genome of the organism, preferably, in association with a transcriptional unit. In vivo functional studies involving a target gene comprising such a recognition site for a protein are then performed; for example, production of each of the two proteins is individually inhibited, for example with antisense RNA or a ribozyme specific for the message encoding the protein, and the effect on the regulation of the target gene is observed. The finding that both proteins are necessary for the proper expression of the target gene provides strong, if circumstantial, evidence that the two components of the heterodimer act in concert to regulate it.

EXAMPLE 6

Nucleic Acid/protein Arrays Comprising a Chimeric Protein Heteromdimer Test Subunit The method described in Example 5, above, is well suited for the discovery of heterodimeric pairing partners and their cognate recognition sites for a protein; however, for each test protein for which pairing partners are sought, a new nucleic acid array must be synthesized, wherein the half site specific for the protein in question is incorporated into every nucleic acid member in association with a spectrum of random half-site sequences, with each random half-site represented by members of a distinct feature, as described above. Given the high cost of array design and synthesis, such a requirement might prove prohibitively expensive in certain situations.

A typical monomer which may form part of a heterodimeric nucleic-acid-binding complex is, itself, a bipartite structure, comprising a dimerization domain and a nucleic acid binding domain (e.g. a DNA binding domain, as defined above). Methods by which these subunits are separated from one another and recombined to form chimeric proteins which retain their capacity to bind nucleic acids are well known in the art (for methods of cloning, expression of cloned genes and protein purification, see Sambrook et al., 1989, *Molecular Cloning. A Laboratory Manual.*, *2nd Edition*, Cold Spring Harbor Laboratory Press, Cold Spring Harbor, N.Y.; Ausubel et al., *Current Protcols in Molecular Biology*, copyright 1987–1994, Current Protocols, copyright 1994–1998, John Wiley & Sons, Inc.). Such chimeric proteins have played a significant role in the discovery of a number of gene trans-regulatory factors, e.g. via the interaction-trap scheme in yeast (Fields and Song, 1989, *Nature*, 340: 245–246). According to the present invention, the dimerization domain of a protein for which pairing partners are sought is fused to the nucleic acid binding domain of a known protein, such as λ 434 Cro. Nucleic acid arrays are synthesized as in Example 5, except that the half site recognized by λ 434 Cro is used, and the procedure of isolating, identifying and characterizing interactions involving candidate pairing partners are performed, all as described above.

EXAMPLE 7

In the Examples above, proteins bound to recognition sites for a protein or proteins present on nucleic acid molecules of arrays according to the invention are labeled using a variety of methods known in the prior art; either they are labeled directly through covalent linkage of radioactive, fluorescent, chemiluminescent or chromogenic substances or of mass-tags, or indirectly via binding to labeled antibodies. The present invention encompasses a procedure in which chimeric proteins, each comprising a DNA binding domain fused in-frame to Green Fluorescent Protein (GFP), are produced by cloning, gene expression and protein isolation methods well known in the art (see Sambrook et al., 1989, supra) and incubated with nucleic acid arrays comprising recognition sites for a protein or proteins produced according to the methods of the invention in order to determine a consensus sequence of a recognition site for a given protein. Since a labeling efficiency of 100% is achieved using this scheme, the amount of fluorescence observed upon upon scanning of the array with an argon laser scanner is directly proportional to the amount of protein bound, not only for the determination of relative binding efficiencies of the protein to different recognition sites for a protein or proteins present on an array of the invention (as described above, using instead other labeling methods combined with a set of buffers of graded salt concentration), but even from protein preparation to protein preparation, allowing for accurate comparative quantitation of the binding efficiencies of different proteins to features of the array, if it is so desired.

Figure 5:
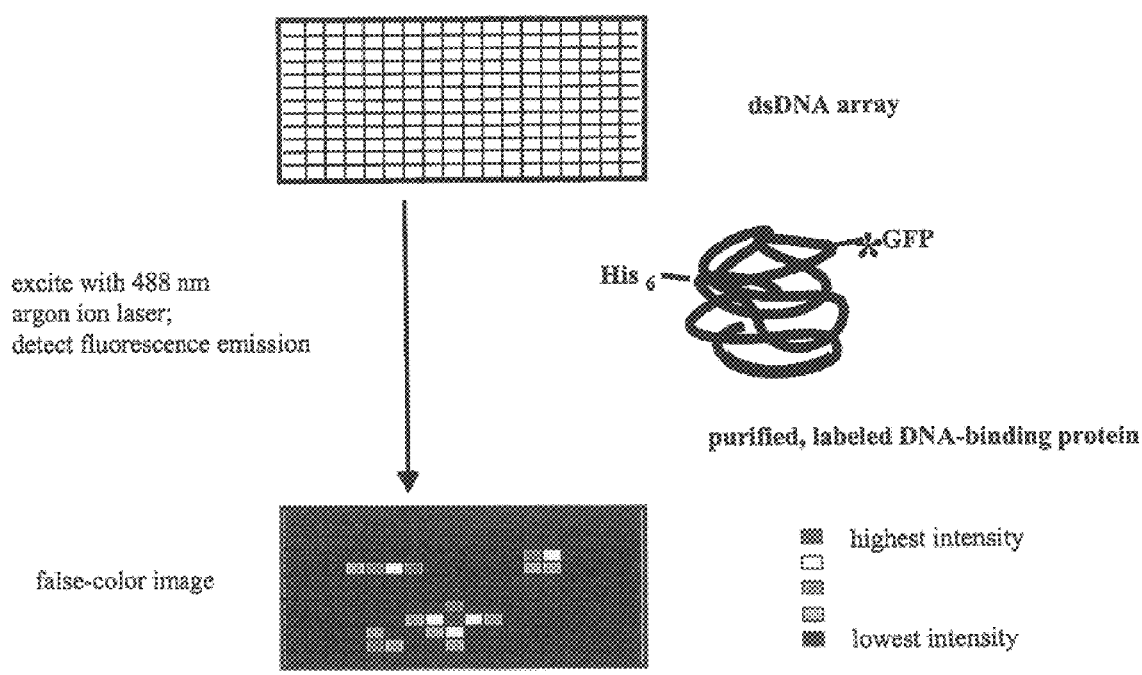
FIG. 5 presents binding of Green Fluorescent Protein to an array of bimolecular, double-stranded DNA molecules on a silica chip, and confocal argon laser scanning to detect the bound protein.

After washing away any unbound fusion protein, the support bearing the array is scanned with the scanning confocal microscope (FIG. 5); the intensity of fluorescence, which is proportional to the amount of protein bound, is correlated with the sequences of nucleic acid molecules, which are known at each position of the scanned surface. The range of sequences to which a protein will bind, as well as the relative efficiency of binding to each, can then be determined. In order to interpret the results, the only source of fluorescence on the chip must be GFP; therefore, the nucleic acid molecules of the array must be unlabeled. The strand extension reaction described above can, if desired, be performed without the use of a fluorescent label; the reaction conditions are identical except that the fluorescein-labeled dATP is omitted, along with the wash step, the purpose of which is to remove unincorporated background fluorescence that ordinarily might interfere with scanning.

USE

The present invention is useful for the production of accurate, high-density, double-stranded nucleic acid arrays comprising recognition sites within a nucleic acid sequence or sequences for a protein or proteins, as well as protein arrays thereof, the sequences of which recognition sites within a nucleic acid sequence for a protein can be determined based upon physical location within the array. The protein arrays provided are useful in a variety of screening or identification procedures. For example, the arrays are useful for testing interactions between a protein and its corresponding recognition site within a nucleic acid sequence for a protein on a nucleic acid molecule. Alternatively, the arrays are useful for examining the effects on binding of a protein to its recognition site within a nucleic acid sequence for a protein of interactions between the protein and a second protein which binds that protein. The arrays also are useful for looking for any nucleic acid seqeunce that is a substrate for a protein-directed enzymatic reaction, such as is mediated by an enzyme including, but not limited to, a nuclease, or a nucleic acid modification enzyme, or isomerase. The invention is also of use in identifying gene trans-regulatory factors. The arrays also are useful for testing any one of a number of protein- or protein/nucleic acid-based biological interactions, such as those protein/protein interactions that occur in signal transduction cascades involving molecules that include, but are not limited to, kinases, proteases or receptor/ligand complexes, as well as identifying proteins, nucleic acids or other substances which might inhibit such interactions. The invention is useful for assaying protein/nucleic acid interactions where the protein or its corresponding recognition site within a nucleic acid sequence for a protein has undergone a mutation, or even where both have been mutated. The invention is of further use in determining the nucleic acid sequence of a recognition site within a nucleic acid sequence for a protein that is recognized by a given protein, or the consensus sequence of a recognition site within a nucleic acid sequence for such a protein or plurality of proteins, e.g., where such a nucleic acid sequence or sequences is/are unknown or incompletely characterized. The invention is of use in determining a consensus amino acid sequence of targeting amino acid sequences of proteins which bind a given recognition site for a protein. The arrays of the invention are additionally useful in identifying genes which may be co-regulated. The arrays are therefore ultimately useful for identifying compositions that are of potential scientific or clinical interest, particularly those with therapeutic potential.

OTHER EMBODIMENTS

Other embodiments will be evident to those of skill in the art. It should be understood that the foregoing description is provided for clarity only and is merely exemplary. The spirit and scope of the present invention are not limited to the above examples, but are encompassed by the following claims.

What is claimed is:

1. A synthetic array comprising:

a solid support, and a plurality of double-stranded nucleic acid molecules, wherein each nucleic acid molecule comprises a first nucleic acid strand linked to the solid support and a second nucleic acid strand which is substantially complementary to the first nucleic acid strand and hybridized to the first nucleic acid strand, wherein the 5' end of the first nucleic acid strand and the 3' end of the second nucleic acid strand are covalently unbound to each other, wherein each nucleic acid molecule comprises a protein recognition site within a double stranded nucleic acid sequence, wherein a protein recognition site within a first nucleic acid molecule is different from a protein recognition site within a second nucleic acid molecule, and a protein is bound to at least one of the nucleic acid molecules, wherein each protein recognition site within a nucleic acid molecule is selected from the group that includes naturally-occurring protein recognition sites, synthetic variants of naturally-occurring protein recognition sites and randomized nucleic acid sequences, and wherein at least one protein recognition site within a nucleic acid molecule comprises first and second half-sites, wherein the first half-site is recognized by a different protein than is the second half-site.

2. The array of claim 1, wherein the 3' end of the first nucleic acid strand is linked to the solid support.

3. The array of claim 1, wherein the 5' end of the second nucleic acid strand is not linked to the solid support.

4. The array of claim 1, wherein the bound protein comprises a detectable label.

5. The array of claim 1, wherein the bound protein is a chimeric protein.

6. The array of claim 5, wherein said chimeric protein comprises a DNA-binding domain fused in-frame with a protein:protein dimerization domain.

7. The array of claim 5, wherein said chimeric protein comprises a DNA-binding domain fused in-frame to Green Fluorescent Protein.

8. The array of claim 1, wherein said solid support is a silica support.

9. The array of claim 1, wherein the first nucleic acid strand is used as the template on which the second nucleic acid strand is produced by enzymatic synthesis.

10. The array of claim 9, wherein the first nucleic acid strand comprises at its 3' end a binding site for an oligonucleotide primer which is used to prime enzymatic synthesis of the second nucleic acid strand, and the first nucleic acid strand comprises at its 5' end a variable sequence.

11. The array of claim 9, wherein said enzymatic synthesis is performed using an enzyme.

12. The array of claim 10, wherein said oligonucleotide primer is between 10 and 30 nucleotides in length.

13. The array of claim 1, wherein the first nucleic acid strand comprises DNA.

14. The array of claim 1, wherein the second nucleic acid strand comprises DNA.

15. The array of claim 1, wherein the first and second nucleic acid strands each comprise from 16 to 60 monomers selected from the group that include ribonucleotides and deoxyribonucleotides.

16. The array of claim 1, wherein the solid support is a silica support and the first and second nucleic acid strands each comprise from 16 to 60 monomers selected from the group that includes ribonucleotides and deoxyribonucleotides.

17. The array of claim 1, wherein at least a portion of said plurality have a second nucleic acid strand that is substantially complementary to- and based-paired with said first strand along the entire length of said first strand.

18. The array of claim 4, wherein the detectable label is radioactive, fluorescent, chemiluminescent, or chromogenic.

19. The array of claim 1, wherein the solid support has surface attaching groups.

20. The array of claim 19, wherein the surface attaching groups are selected from the group consisting of amine, hydroxyl, thiol, and carboxyl groups.

21. The array of claim 5, wherein the chimeric protein comprises a DNA-binding domain fused in frame with a protein:protein dimerization domain.

22. The array of claim 5, wherein the chimeric protein comprises a DNA-binding domain fused in frame to Green Fluorescent Protein.

* * * * *

SEQUENCE LISTING

<160> NUMBER OF SEQ ID NOS: 43

<210> SEQ ID NO 1
<211> LENGTH: 16
<212> TYPE: DNA
<213> ORGANISM: Primer for second strand synthesis

<400> SEQUENCE: 1
tccacactct ccaaca                                                    16

<210> SEQ ID NO 2
<211> LENGTH: 16
<212> TYPE: DNA
<213> ORGANISM: Primer for second strand synthesis

<400> SEQUENCE: 2
ggaccctttg acttga                                                    16

<210> SEQ ID NO 3
<211> LENGTH: 17
<212> TYPE: DNA
<213> ORGANISM: Escherichia coli

<400> SEQUENCE: 3
atctggtacg accagat                                                   17

<210> SEQ ID NO 4
<211> LENGTH: 22
<212> TYPE: DNA
<213> ORGANISM: Escherichia coli

<400> SEQUENCE: 4
aaatgtgatc tagatcacat tt                                             22

<210> SEQ ID NO 5
<211> LENGTH: 13
<212> TYPE: DNA
<213> ORGANISM: Escherichia coli
<220> FEATURE:
<221> NAME/KEY: misc_feature
<222> LOCATION: (4)..(9)
<223> OTHER INFORMATION: n is a, c, g, or t

<400> SEQUENCE: 5
aacnnnnnng tgc                                                       13

<210> SEQ ID NO 6
<211> LENGTH: 14
<212> TYPE: DNA
<213> ORGANISM: Escherichia coli

<400> SEQUENCE: 6
acaatatata ttgt                                                      14

<210> SEQ ID NO 7
<211> LENGTH: 13
<212> TYPE: DNA
<213> ORGANISM: Escherichia coli
<220> FEATURE:
<221> NAME/KEY: misc_feature
<222> LOCATION: (7)..(7)
<223> OTHER INFORMATION: n is a, c, g, or t

```
<400> SEQUENCE: 7
agaatwnwat tct                                                13

<210> SEQ ID NO 8
<211> LENGTH: 14
<212> TYPE: DNA
<213> ORGANISM: Escherichia coli

<400> SEQUENCE: 8
ataaaacgtt ttat                                               14

<210> SEQ ID NO 9
<211> LENGTH: 16
<212> TYPE: DNA
<213> ORGANISM: Escherichia coli
<220> FEATURE:
<221> NAME/KEY: misc_feature
<222> LOCATION: (7)..(10)
<223> OTHER INFORMATION: n is a, c, g, or t

<400> SEQUENCE: 9
attgatnnnn atcaat                                             16

<210> SEQ ID NO 10
<211> LENGTH: 14
<212> TYPE: DNA
<213> ORGANISM: Escherichia coli
<220> FEATURE:
<221> NAME/KEY: misc_feature
<222> LOCATION: (5)..(10)
<223> OTHER INFORMATION: n is a, c, g, or t

<400> SEQUENCE: 10
atygnnnnnn crat                                               14

<210> SEQ ID NO 11
<211> LENGTH: 27
<212> TYPE: DNA
<213> ORGANISM: Escherichia coli
<220> FEATURE:
<221> NAME/KEY: misc_feature
<222> LOCATION: (6)..(23)
<223> OTHER INFORMATION: n is a, c, g, or t

<400> SEQUENCE: 11 cccccnnnn nnnnnnnnnn nnncccc                                  27

<210> SEQ ID NO 12
<211> LENGTH: 14
<212> TYPE: DNA
<213> ORGANISM: Escherichia coli

<400> SEQUENCE: 12
ccgaaacgtt tcgg                                               14

<210> SEQ ID NO 13
<211> LENGTH: 21
<212> TYPE: DNA
<213> ORGANISM: Escherichia coli

<400> SEQUENCE: 13
cgcartattc aygytgrtga t                                       21

<210> SEQ ID NO 14
<211> LENGTH: 17
```

```
<212> TYPE: DNA
<213> ORGANISM: Escherichia coli
<220> FEATURE:
<221> NAME/KEY: misc_feature
<222> LOCATION: (6)..(12)
<223> OTHER INFORMATION: n is a, c, g, or t

<400> SEQUENCE: 14
ctggcnnnnn nnttgca                                                17

<210> SEQ ID NO 15
<211> LENGTH: 18
<212> TYPE: DNA
<213> ORGANISM: Escherichia coli

<400> SEQUENCE: 15
ctktcatawa wctgtcay                                               18

<210> SEQ ID NO 16
<211> LENGTH: 19
<212> TYPE: DNA
<213> ORGANISM: Escherichia coli

<400> SEQUENCE: 16
gaaaataatt cttatttcg                                              19

<210> SEQ ID NO 17
<211> LENGTH: 13
<212> TYPE: DNA
<213> ORGANISM: Escherichia coli
<220> FEATURE:
<221> NAME/KEY: misc_feature
<222> LOCATION: (6)..(6)
<223> OTHER INFORMATION: n is a, c, g, or t
<221> NAME/KEY: misc_feature
<222> LOCATION: (9)..(9)
<223> OTHER INFORMATION: n is a, c, g, or t

<400> SEQUENCE: 17 gatctntttnt ttt                                                   13

<210> SEQ ID NO 18
<211> LENGTH: 14
<212> TYPE: DNA
<213> ORGANISM: Escherichia coli
<220> FEATURE:
<221> NAME/KEY: misc_feature
<222> LOCATION: (5)..(11)
<223> OTHER INFORMATION: n is a, c, g, or t

<400> SEQUENCE: 18
gcacnnnnnn ncaa                                                   14

<210> SEQ ID NO 19
<211> LENGTH: 16
<212> TYPE: DNA
<213> ORGANISM: Escherichia coli
<220> FEATURE:
<221> NAME/KEY: misc_feature
<222> LOCATION: (7)..(7)
<223> OTHER INFORMATION: n is a, c, g, or t
<221> NAME/KEY: misc_feature
<222> LOCATION: (10)..(10)
<223> OTHER INFORMATION: n is a, c, g, or t

<400> SEQUENCE: 19
gtgtaancgn ttacac                                                 16
```

```
<210> SEQ ID NO 20
<211> LENGTH: 29
<212> TYPE: DNA
<213> ORGANISM: Escherichia coli
<220> FEATURE:
<221> NAME/KEY: misc_feature
<222> LOCATION: (7)..(24)
<223> OTHER INFORMATION: n is a, c, g, or t

<400> SEQUENCE: 20
gttaagnnnn nnnnnnnnnn nnnncgtcc                                29

<210> SEQ ID NO 21
<211> LENGTH: 20
<212> TYPE: DNA
<213> ORGANISM: Escherichia coli

<400> SEQUENCE: 21
tactgtatat atatacagta                                          20

<210> SEQ ID NO 22
<211> LENGTH: 17
<212> TYPE: DNA
<213> ORGANISM: Escherichia coli
<220> FEATURE:
<221> NAME/KEY: misc_feature
<222> LOCATION: (9)..(9)
<223> OTHER INFORMATION: n is a, c, g, or t

<400> SEQUENCE: 22
tagtaaaant tttacta                                             17

<210> SEQ ID NO 23
<211> LENGTH: 17
<212> TYPE: DNA
<213> ORGANISM: Escherichia coli
<220> FEATURE:
<221> NAME/KEY: misc_feature
<222> LOCATION: (9)..(9)
<223> OTHER INFORMATION: n is a, c, g, or t

<400> SEQUENCE: 23
tatcaccgng cgtgata                                             17

<210> SEQ ID NO 24
<211> LENGTH: 18
<212> TYPE: DNA
<213> ORGANISM: Escherichia coli
<220> FEATURE:
<221> NAME/KEY: misc_feature
<222> LOCATION: (6)..(13)
<223> OTHER INFORMATION: n is a, c, g, or t

<400> SEQUENCE: 24
tatccnnnnn nnnggata                                            18

<210> SEQ ID NO 25
<211> LENGTH: 13
<212> TYPE: DNA
<213> ORGANISM: Escherichia coli
<220> FEATURE:
<221> NAME/KEY: misc_feature
<222> LOCATION: (5)..(9)
<223> OTHER INFORMATION: n is a, c, g, or t

<400> SEQUENCE: 25
tgaannnnnt tca                                                 13
```

```
<210> SEQ ID NO 26
<211> LENGTH: 12
<212> TYPE: DNA
<213> ORGANISM: Escherichia coli

<400> SEQUENCE: 26
tgaaacgttt ca                                                           12

<210> SEQ ID NO 27
<211> LENGTH: 14
<212> TYPE: DNA
<213> ORGANISM: Escherichia coli
<220> FEATURE:
<221> NAME/KEY: misc_feature
<222> LOCATION: (7)..(8)
<223> OTHER INFORMATION: n is a, c, g, or t

<400> SEQUENCE: 27
tgaatannta ttca                                                         14

<210> SEQ ID NO 28
<211> LENGTH: 17
<212> TYPE: DNA
<213> ORGANISM: Escherichia coli
<220> FEATURE:
<221> NAME/KEY: misc_feature
<222> LOCATION: (9)..(9)
<223> OTHER INFORMATION: n is a, c, g, or t

<400> SEQUENCE: 28
tgcaccwwnw wggtgca                                                      17

<210> SEQ ID NO 29
<211> LENGTH: 18
<212> TYPE: DNA
<213> ORGANISM: Escherichia coli
<220> FEATURE:
<221> NAME/KEY: misc_feature
<222> LOCATION: (7)..(12)
<223> OTHER INFORMATION: n is a, c, g, or t

<400> SEQUENCE: 29
tgtaaannnn nntttaca                                                     18

<210> SEQ ID NO 30
<211> LENGTH: 20
<212> TYPE: DNA
<213> ORGANISM: Escherichia coli
<220> FEATURE:
<221> NAME/KEY: misc_feature
<222> LOCATION: (6)..(6)
<223> OTHER INFORMATION: n is a, c, g, or t
<221> NAME/KEY: misc_feature
<222> LOCATION: (15)..(15)
<223> OTHER INFORMATION: n is a, c, g, or t

<400> SEQUENCE: 30
tgttangyya trrcntaaca                                                   20

<210> SEQ ID NO 31
<211> LENGTH: 17
<212> TYPE: DNA
<213> ORGANISM: Escherichia coli
<220> FEATURE:
<221> NAME/KEY: misc_feature
<222> LOCATION: (2)..(2)
<223> OTHER INFORMATION: n is a, c, g, or t
```

```
<221> NAME/KEY: misc_feature
<222> LOCATION: (8)..(13)
<223> OTHER INFORMATION: n is a, c, g, or t

<400> SEQUENCE: 31
tntggacnnn nnngcta                                                    17

<210> SEQ ID NO 32
<211> LENGTH: 28
<212> TYPE: DNA
<213> ORGANISM: Escherichia coli
<220> FEATURE:
<221> NAME/KEY: misc_feature
<222> LOCATION: (7)..(22)
<223> OTHER INFORMATION: n is a, c, g, or t

<400> SEQUENCE: 32
ttgacannnn nnnnnnnnnn nntataat                                        28

<210> SEQ ID NO 33
<211> LENGTH: 29
<212> TYPE: DNA
<213> ORGANISM: Escherichia coli
<220> FEATURE:
<221> NAME/KEY: misc_feature
<222> LOCATION: (7)..(24)
<223> OTHER INFORMATION: n is a, c, g, or t

<400> SEQUENCE: 33
ttgacannnn nnnnnnnnnn nnntataat                                       29

<210> SEQ ID NO 34
<211> LENGTH: 30
<212> TYPE: DNA
<213> ORGANISM: Escherichia coli
<220> FEATURE:
<221> NAME/KEY: misc_feature
<222> LOCATION: (7)..(24)
<223> OTHER INFORMATION: n is a, c, g, or t

<400> SEQUENCE: 34
ttgacannnn nnnnnnnnnn nnnntataat                                      30

<210> SEQ ID NO 35
<211> LENGTH: 14
<212> TYPE: DNA
<213> ORGANISM: Escherichia coli
<220> FEATURE:
<221> NAME/KEY: misc_feature
<222> LOCATION: (7)..(8)
<223> OTHER INFORMATION: n is a, c, g, or t

<400> SEQUENCE: 35
ttgawcnngw tcat                                                       14

<210> SEQ ID NO 36
<211> LENGTH: 14
<212> TYPE: DNA
<213> ORGANISM: Escherichia coli
<220> FEATURE:
<221> NAME/KEY: misc_feature
<222> LOCATION: (5)..(10)
<223> OTHER INFORMATION: n is a, c, g, or t

<400> SEQUENCE: 36
ttgcnnnnnn gcaa                                                       14
```

```
<210> SEQ ID NO 37
<211> LENGTH: 14
<212> TYPE: DNA
<213> ORGANISM: Escherichia coli
<220> FEATURE:
<221> NAME/KEY: misc_feature
<222> LOCATION: (5)..(10)
<223> OTHER INFORMATION: n is a, c, g, or t

<400> SEQUENCE: 37
ttgcnnnnnn ttgc                                                   14

<210> SEQ ID NO 38
<211> LENGTH: 16
<212> TYPE: DNA
<213> ORGANISM: Escherichia coli

<400> SEQUENCE: 38
ttgtgagcgc tcacaa                                                 16

<210> SEQ ID NO 39
<211> LENGTH: 17
<212> TYPE: DNA
<213> ORGANISM: Escherichia coli
<220> FEATURE:
<221> NAME/KEY: misc_feature
<222> LOCATION: (9)..(9)
<223> OTHER INFORMATION: n is a, c, g, or t

<400> SEQUENCE: 39
ttgtgagcng ctcacaa                                                17

<210> SEQ ID NO 40
<211> LENGTH: 18
<212> TYPE: DNA
<213> ORGANISM: Escherichia coli

<400> SEQUENCE: 40
ttgttagaat tctaacaa                                               18

<210> SEQ ID NO 41
<211> LENGTH: 13
<212> TYPE: DNA
<213> ORGANISM: Escherichia coli
<220> FEATURE:
<221> NAME/KEY: misc_feature
<222> LOCATION: (7)..(7)
<223> OTHER INFORMATION: n is a, c, g, or t

<400> SEQUENCE: 41
tttagcngct aaa                                                    13

<210> SEQ ID NO 42
<211> LENGTH: 13
<212> TYPE: DNA
<213> ORGANISM: Escherichia coli
<220> FEATURE:
<221> NAME/KEY: misc_feature
<222> LOCATION: (7)..(13)
<223> OTHER INFORMATION: n is a, c, g, or t

<400> SEQUENCE: 42
watcaannnn ttr                                                    13

<210> SEQ ID NO 43
<211> LENGTH: 20
<212> TYPE: DNA
```

-continued

```
<213> ORGANISM: Escherichia coli

<400> SEQUENCE: 43
watgttcgwt awcgaacatw                                          20
```